US008784360B2

(12) United States Patent
Nelson

(10) Patent No.: US 8,784,360 B2
(45) Date of Patent: Jul. 22, 2014

(54) CATHETER SYSTEMS HAVING FLOW RESTRICTORS

(75) Inventor: Brian D. Nelson, Birchwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 809 days.

(21) Appl. No.: 12/691,241

(22) Filed: Jan. 21, 2010

(65) Prior Publication Data

US 2010/0217196 A1 Aug. 26, 2010

Related U.S. Application Data

(60) Provisional application No. 61/146,231, filed on Jan. 21, 2009.

(51) Int. Cl.
*A61M 1/00* (2006.01)

(52) U.S. Cl.
USPC .............................. 604/30; 604/246

(58) Field of Classification Search
USPC ............................ 604/246, 30, 284
See application file for complete search history.

(56) References Cited

U.S. PATENT DOCUMENTS

| 3,626,959 | A | 12/1971 | Santomieri |
| 3,671,979 | A | 6/1972 | Moulopoulos |
| 3,951,147 | A | 4/1976 | Tucker et al. |
| 4,176,683 | A | 12/1979 | Leibinsohn |
| 4,397,335 | A | 8/1983 | Doblar et al. |
| 4,411,292 | A | 10/1983 | Schiller |
| 4,550,748 | A | 11/1985 | Nunez |
| 4,759,752 | A | 7/1988 | Stöber |
| 4,798,226 | A | 1/1989 | Struth |
| 4,834,704 | A | 5/1989 | Reinicke |

(Continued)

FOREIGN PATENT DOCUMENTS

| EP | 0287 247 A2 | 10/1988 |
| EP | 0287 247 A3 | 10/1988 |

(Continued)

OTHER PUBLICATIONS

U.S. Appl. No. 11/112,077, filed Apr. 22, 2005, Olsen et al.

(Continued)

*Primary Examiner* — Kevin C Sirmons
*Assistant Examiner* — Deanna K Hall
(74) *Attorney, Agent, or Firm* — Mueting, Raasch & Gebhardt, P.A.

(57) ABSTRACT

Infusion catheter systems and methods are described herein that incorporate flow restrictors to balance flow to multiple target sites serviced by delivery catheters. Fluids may be delivered to the target sites using multiple separate delivery catheters or through multiple separate lumens located in the same delivery catheter. Flow balancing may be performed between multiple catheters that are fed from a single fluid source, between multiple separate lumens in a single delivery catheter that are also fed from a single fluid source. Multiple catheters may be fluidly connected to one or more flow restrictors housed within an anchor or in another embodiment, a catheter may be fluidly connected to a restrictor housed in one anchor and another catheter fluidly connected to a second anchor wherein each of the restrictors is also fluidly connected to a single fluid source. Two or more anchors may be fed from a single source, with each anchor containing one or more flow restrictors that feed one, two or more delivery catheters that are attached to each of the anchors (i.e., each anchor may be attached to one, two, three, or more delivery catheters).

10 Claims, 14 Drawing Sheets

(56) References Cited

U.S. PATENT DOCUMENTS

| | | |
|---|---|---|
| 5,006,997 A | 4/1991 | Reich |
| 5,279,544 A | 1/1994 | Gross et al. |
| 5,342,298 A | 8/1994 | Michaels et al. |
| 5,395,352 A | 3/1995 | Penny |
| 5,531,684 A | 7/1996 | Ensminger et al. |
| 5,558,640 A | 9/1996 | Pfeiler et al. |
| 5,605,545 A | 2/1997 | Nowosielski et al. |
| 5,746,722 A | 5/1998 | Pohndorf et al. |
| 5,820,589 A | 10/1998 | Torgerson et al. |
| 5,893,838 A | 4/1999 | Daoud et al. |
| 5,899,873 A | 5/1999 | Jones et al. |
| 5,928,195 A | 7/1999 | Malamud et al. |
| 5,999,857 A | 12/1999 | Weijand et al. |
| 6,179,806 B1 | 1/2001 | Sansoucy |
| 6,203,523 B1 | 3/2001 | Haller et al. |
| 6,551,290 B1 | 4/2003 | Elsberry et al. |
| 6,585,681 B2 | 7/2003 | Brugger et al. |
| 6,689,085 B1 | 2/2004 | Rubenstein et al. |
| 6,749,581 B2 | 6/2004 | Thompson et al. |
| 6,893,429 B2 | 5/2005 | Petersen |
| 6,945,969 B1 | 9/2005 | Morris et al. |
| 7,217,251 B2 | 5/2007 | Olsen et al. |
| 7,766,860 B2 * | 8/2010 | Olsen et al. ............... 604/34 |
| 2002/0107471 A1 | 8/2002 | Thompson et al. |
| 2004/0199128 A1 | 10/2004 | Morris et al. |
| 2005/0075624 A1 | 4/2005 | Miesel |
| 2005/0090799 A1 | 4/2005 | Morris |
| 2005/0241387 A1 | 11/2005 | Miesel et al. |
| 2005/0245858 A1 | 11/2005 | Miesel et al. |
| 2005/0245867 A1 | 11/2005 | Olsen et al. |
| 2005/0245887 A1 | 11/2005 | Olsen et al. |
| 2007/0043335 A1 | 2/2007 | Olsen et al. |
| 2009/0187149 A1 | 7/2009 | Nelson |

FOREIGN PATENT DOCUMENTS

| | | |
|---|---|---|
| EP | 0 361 662 A1 | 4/1990 |
| EP | 0287 247 B1 | 8/1992 |
| EP | 0 361 662 B1 | 6/1993 |
| EP | 0 564 321 A2 | 10/1993 |
| EP | 0 564 321 A3 | 1/1994 |
| EP | 0 564 321 B1 | 12/1996 |
| EP | 0 873 762 A2 | 10/1998 |
| EP | 0 873 762 A3 | 6/1999 |
| EP | 0 968 732 A2 | 1/2000 |
| EP | 0 968 732 A3 | 1/2001 |
| EP | 0 873 762 B1 | 12/2003 |
| EP | 0 968 732 B1 | 9/2007 |
| WO | WO 98/21419 A1 | 5/1998 |
| WO | WO 2004/026373 A1 | 4/2004 |

OTHER PUBLICATIONS

International Search Report and Written Opinion for PCT/US2010/021591; 9 pgs.

U.S. Appl. No. 12/357,120, filed Jan. 21, 2009, Nelson.

U.S. Appl. No. 61/146,231, filed Jan. 21, 2009, Nelson.

* cited by examiner

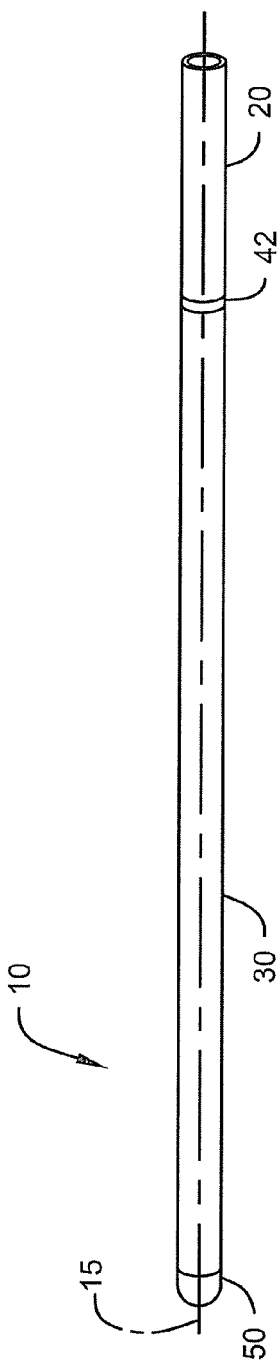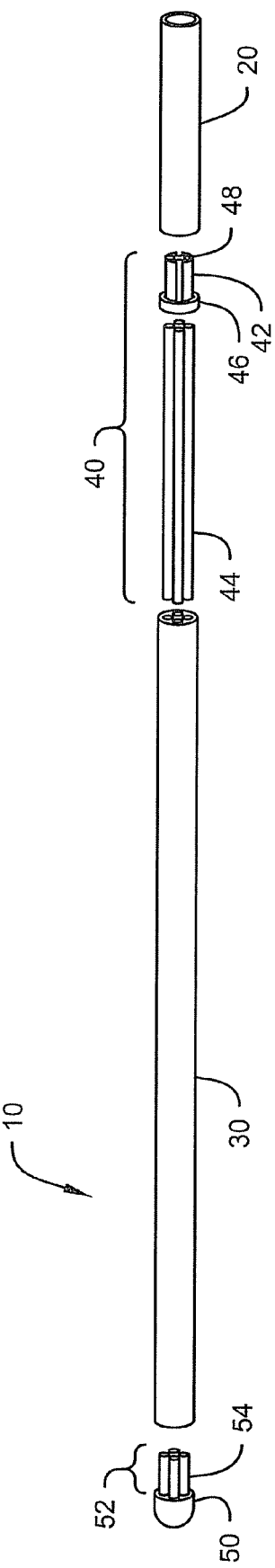

CATHETER SYSTEMS HAVING FLOW RESTRICTORS

RELATED APPLICATION

The present application claims the benefit under 35 U.S.C. §119 of U.S. Provisional Patent Application No. 61/146,231 titled CATHETER SYSTEMS HAVING FLOW RESTRICTORS filed on Jan. 21, 2009, which is hereby incorporated by reference in its entirety.

Implantable medical devices are described herein and, more particularly, infusion catheter systems are described herein which incorporate two or more fluid pathways that are flow-balanced by the use of two or more flow restrictors.

Implantable infusion systems are used to provide programmable long-term delivery of a therapeutic agent, e.g., infusate drug, to a target site such as the brain or the spinal canal or epidural space. These systems typically include a pump implanted at a remote location, e.g., within the abdominal or chest cavity, and a catheter tunneled from the pump to the target site. A drug may be delivered from a reservoir in the pump to the target site via the catheter.

Some therapies, e.g., treatment of many neurological diseases, may benefit from infusion of a therapeutic agent to multiple locations within the body. For instance, for the treatment of Parkinson's Disease, it may be beneficial to deliver a substance, e.g., Glial Derived Neurotrophic Factor (GDNF), to both hemispheres of the brain (bilaterally). Infusing a drug to such multiple target sites can be accomplished by using multiple infusion systems, e.g., a separate pump and catheter system with a single exit hole for each target site. However, multiple systems result in not only increased costs and patient invasiveness (as compared to single target site systems), but also increased complexity that is inherent in such multiple systems.

SUMMARY

Catheter systems and methods are described herein that incorporate flow restrictors to balance flow to multiple target sites. Fluids may be delivered to the target sites using multiple separate delivery catheters or through multiple separate lumens located in the same delivery catheter. In either case, the catheter system includes multiple fluid pathways in which flow balancing is desired. That flow balancing may be performed between multiple catheters that are fed from a single fluid source, between multiple separate lumens in a single delivery catheter that are also fed from a single fluid source. In some embodiments, multiple catheters may be fluidly connected to one or more flow restrictors housed within an anchor or in another embodiment, a catheter may be fluidly connected to a restrictor housed in one anchor and another catheter fluidly connected to a second anchor wherein each of the restrictors is also fluidly connected to a single fluid source. In some embodiments, two or more anchors may be fed from a single source, with each anchor containing one or more flow restrictors that feed one, two or more delivery catheters that are attached to each of the anchors (i.e., each anchor may be attached to one, two, three, or more delivery catheters).

In some instances, catheter systems and methods described herein may have a main or serial line that feeds or supplies fluid from a single source to multiple parallel lines, with the system including a branch point between the serial line and the parallel lines. The multiple parallel lines may be contained within a single delivery catheter that includes multiple separate lumens feeding different target sites. Alternatively, the multiple parallel lines may be provided in the form of separate delivery catheters feeding different target sites. The flow restrictors may preferably be located at the branch point, i.e., the point at which the flow is converted to parallel flow lines from a common or supply flow line. That branch point may, in some embodiments, be located in an anchor or anchors used to hold the delivery catheters in place when implanted.

Some embodiments of the systems and methods described herein may include flow restrictors positioned in the anchors used to secure delivery catheters implanted in a patient and positioned to deliver fluids to a predetermined target site in the patient. The flow restrictors are used to restrict flow to the different delivery catheters to control flow to those delivery catheters (e.g., to balance the flow to the different delivery catheters). Positioning the flow restrictors in the anchors may be advantageous because the flow restrictors may have a form factor that may be more amenable to placement in the anchors rather than in the delivery catheters. In addition, replacement of flow restrictors that may become clogged or otherwise impaired or replacement of the flow restrictors to adjust fluid flow rates into the different delivery catheters may be more easily accomplished by locating the flow restrictors in anchors that may be more easily accessed after initial deployment of the system in a patient.

In one aspect, some embodiments of an infusion catheter system as described herein include a first delivery catheter comprising a proximal end and a distal end, wherein the first delivery catheter comprises a first delivery lumen extending from the proximal end of the first delivery catheter to a first infusion location located distally from the proximal end of the first delivery catheter, wherein the first infusion location comprises an opening through which fluid moving distally through the first delivery lumen exits the first delivery catheter; a second delivery catheter comprising a proximal end and a distal end, wherein the second delivery catheter comprises a second delivery lumen extending from the proximal end of the second delivery catheter to a second infusion location located distally from the proximal end of the second delivery catheter, wherein the second infusion location comprises an opening through which fluid moving distally through the second delivery lumen exits the second delivery catheter; a connector comprising a supply port, a first exit port in fluid communication with the first delivery lumen in the first delivery catheter, and a second exit port in fluid communication with the second delivery lumen in the second delivery catheter, wherein fluid entering the connector through the supply port exits the connector through either the first exit port or the second exit port; a first flow restrictor located between the first exit port of the connector and the first delivery lumen such that fluid flowing through the first exit port into the first delivery lumen must pass through the first flow restrictor; a second flow restrictor located between the second exit port of the connector and the second delivery lumen such that fluid flowing through the second exit port into the second delivery lumen must pass through the second flow restrictor; and an anchor comprising an anchor body operable to secure to tissue at a selected location, wherein the anchor body comprises engagement surfaces configured to receive and immobilize the first delivery catheter as it passes through the anchor, wherein the first flow restrictor is housed in the anchor body.

In some embodiments of the infusion catheter systems described herein, the first flow restrictor is located in a first cavity in the anchor body. In some embodiments, the anchor comprises a cap covering the first cavity on a top surface of the anchor body.

In some embodiments of the infusion catheter systems described herein, the second flow restrictor is located in a second cavity in the anchor body. In some embodiments, the anchor comprises a first cap covering the first cavity on a top surface of the anchor body; and further wherein the anchor comprises a second cap covering the second cavity on the top surface of the anchor body.

In some embodiments of the infusion catheter systems described herein, the connector is located within a cavity in the anchor body.

In some embodiments of the infusion catheter systems described herein, the first flow restrictor comprises a housing that comprises a pair of opposed major exterior surfaces, wherein one major exterior surface of the opposed major exterior surfaces faces a top surface of the anchor body and the other major exterior surface faces a bottom surface of the anchor body. In some embodiments, the first flow restrictor comprises a first substrate member and a second substrate member in the housing, the first substrate member having a top surface and the second substrate member having a bottom surface, the bottom surface of the second substrate member positioned against the top surface of the first substrate member to form a chip assembly; one of the top surface and the bottom surface having a channel formed therein; and the chip assembly having an inlet port in fluid communication with the first exit port of the connector and an outlet port in fluid connection with the first delivery lumen so that fluid flowing through the first exit port of the connector into the first delivery lumen must pass through the channel in the first flow restrictor.

In some embodiments of the infusion catheter systems described herein, the first delivery catheter and the second delivery catheter form a first pair of delivery catheters attached to the anchor, and wherein the system further comprises a second pair of delivery catheters, and wherein a separate flow restrictor is located in a fluid supply path to the second pair of delivery catheters.

In some embodiments of the infusion catheter systems described herein, the system further comprises a second anchor that comprises a second anchor body operable to secure to tissue at a selected location, wherein the second anchor body comprises engagement surfaces configured to receive and immobilize the second delivery catheter as it passes through the second anchor, and wherein the second flow restrictor is housed in the second anchor body. In some embodiments, the second flow restrictor is located in a cavity in the second anchor body. In some embodiments, the second anchor comprises a cap covering the cavity on a top surface of the second anchor body.

In some embodiments of the infusion catheter systems described herein, the first flow restrictor comprises a disk-shaped body that comprises an orifice formed therethrough, wherein the disk-shaped body is located between an inlet port and an exit port of the first flow restrictor such that fluid flowing through the first flow restrictor must pass through the orifice.

In some embodiments of the infusion catheter systems described herein, the anchor comprises a burr hole anchor operable to secure to bone surrounding a burr hole.

In a second aspect, some embodiments of the infusion catheter systems described herein include a first delivery catheter comprising a proximal end and a distal end, wherein the first delivery catheter comprises a first delivery lumen extending from the proximal end of the first delivery catheter to a first infusion location located distally from the proximal end of the first delivery catheter, wherein the first infusion location comprises an opening through which fluid moving distally through the first delivery lumen exits the first delivery catheter; a second delivery catheter comprising a proximal end and a distal end, wherein the second delivery catheter comprises a second delivery lumen extending from the proximal end of the second delivery catheter to a second infusion location located distally from the proximal end of the second delivery catheter, wherein the second infusion location comprises an opening through which fluid moving distally through the second delivery lumen exits the second delivery catheter; a connector comprising a supply port, a first exit port in fluid communication with the first delivery lumen in the first delivery catheter, and a second exit port in fluid communication with the second delivery lumen in the second delivery catheter, wherein fluid entering the connector through the supply port exits the connector through either the first exit port or the second exit port; a first flow restrictor located between the first exit port of the connector and the first delivery lumen such that fluid flowing through the first exit port into the first delivery lumen must pass through the first flow restrictor; a second flow restrictor located between the second exit port of the connector and the second delivery lumen such that fluid flowing through the second exit port into the second delivery lumen must pass through the second flow restrictor; a first anchor comprising a first anchor body operable to secure to tissue at a selected location, wherein the first anchor body comprises engagement surfaces configured to immobilize the first delivery catheter relative to the first anchor, wherein the first flow restrictor is housed in the first anchor body; and a second anchor comprising a second anchor body operable to secure to tissue at a selected location, wherein the second anchor body comprises engagement surfaces configured to immobilize the second delivery catheter relative to the second anchor, wherein the second flow restrictor is housed in the second anchor body; and a supply tube connecting the second exit port of the connector to the second flow restrictor, wherein fluid flowing from the supply port of the connector to the second flow restrictor in the second anchor must pass through the supply lumen.

In some embodiments of the second aspect of the infusion catheter systems described herein, the connector is attached to the first anchor.

In some embodiments of the second aspect of the infusion catheter systems described herein, the system further comprising a third delivery catheter comprising a proximal end and a distal end, wherein the third delivery catheter comprises a third delivery lumen extending from the proximal end of the third delivery catheter to an infusion location located distally from the proximal end of the third delivery catheter, wherein the third infusion location comprises an opening through which fluid moving distally through the third delivery lumen exits the third delivery catheter; wherein the connector comprises a third exit port in fluid communication with the third delivery lumen in the third delivery catheter wherein fluid entering the connector through the supply port exits the connector through either the first exit port, the second exit port, or the third exit port; and a third flow restrictor located between the third exit port of the connector and the third delivery lumen such that fluid flowing through the third exit port into the third delivery lumen must pass through the third flow restrictor; wherein the third flow restrictor is located in the first anchor.

In some embodiments of the second aspect of the infusion catheter systems described herein, the first anchor comprises a burr hole anchor operable to secure to bone surrounding a burr hole.

In a third aspect, some embodiments of the infusion catheter systems described herein include a first delivery catheter comprising a proximal end and a distal end, wherein the first delivery catheter comprises a first delivery lumen extending from the proximal end of the first delivery catheter to a first infusion location located distally from the proximal end of the first delivery catheter, wherein the first infusion location comprises an opening through which fluid moving distally through the first delivery lumen exits the first delivery catheter; a second delivery catheter comprising a proximal end and a distal end, wherein the second delivery catheter comprises a second delivery lumen extending from the proximal end of the second delivery catheter to a second infusion location located distally from the proximal end of the second delivery catheter, wherein the second infusion location comprises an opening through which fluid moving distally through the second delivery lumen exits the second delivery catheter; a connector comprising a supply port, a first exit port, and a second exit port, wherein the first exit port is in fluid communication with the first delivery lumen in the first delivery catheter and the second exit port is in fluid communication with the second delivery lumen in the second delivery catheter, wherein fluid entering the connector through the supply port exits the connector through either the first exit port or the second exit port; a first restrictor comprising a disk-shaped body that comprises an orifice formed therethrough, wherein the disk-shaped body is located between the first exit port of the connector and the first delivery lumen such that fluid flowing through the first exit port into the first delivery lumen must pass through the orifice in the first restrictor; and a second restrictor comprising a disk-shaped body that comprises an orifice formed therethrough, wherein the disk-shaped body is located between the second exit port of the connector and the second delivery lumen such that fluid flowing through the second exit port into the second delivery lumen must pass through the orifice in the second restrictor. In some embodiments, the orifices in the first restrictor and the second restrictor comprise flow-matched orifices.

In a fourth aspect, some embodiments of the infusion catheter systems described herein include a delivery catheter comprising a proximal end and a distal end, wherein the delivery catheter comprises an elongate body extending from the proximal end to the distal end; a first fluid pathway extending from the proximal end of the delivery catheter to a first infusion location located distally from the proximal end, wherein the first infusion location comprises an opening through which fluid moving distally through the first fluid pathway exits the delivery catheter; a second fluid pathway extending from a proximal end of the delivery catheter to a second infusion location located distally from the proximal end, wherein the second infusion location comprises an opening through which fluid moving distally through the second fluid pathway exits the delivery catheter, wherein the first fluid pathway and the second fluid pathway are separate and distinct from each other; a supply tube comprising a proximal end and a distal end, wherein a supply lumen extends from the proximal end of the supply tube to the distal end of the supply tube; and a flow restrictor element operably attaching the supply tube and the delivery catheter, wherein the flow restrictor element comprises a first capillary tube extending into the first fluid pathway of the delivery catheter and a second capillary tube extending into the second fluid pathway of the delivery catheter, wherein fluid flowing from the supply lumen into the first fluid pathway must pass through the first capillary tube and wherein fluid flowing from the supply lumen into the second fluid pathway must pass through the second capillary tube.

In some embodiments of the fourth aspect of the infusion catheter systems described herein, the first capillary tube and the second capillary tube comprise flow-matched capillary tubes.

In some embodiments of the fourth aspect of the infusion catheter systems described herein, the delivery catheter comprises a delivery catheter length as measured between the proximal end and the distal end of the delivery catheter, and wherein the first capillary tube extends along a length that is one half or less than a delivery catheter length as measured between the proximal end and the distal end of the delivery catheter.

In a fifth aspect, some embodiments of the infusion catheter systems described herein include a feed catheter comprising a proximal end and a distal end, wherein the feed catheter comprises an elongate body extending from the proximal end to the distal end; a first fluid pathway extending from the proximal end of the feed catheter to a first feed opening located distally from the proximal end, wherein the first feed opening comprises an opening through which fluid moving distally through the first fluid pathway exits the feed catheter; a second fluid pathway extending from a proximal end of the feed catheter to a second feed opening located distally from the proximal end, wherein the second feed opening comprises an opening through which fluid moving distally through the second fluid pathway exits the feed catheter, wherein the first fluid pathway and the second fluid pathway are separate and distinct from each other; a first delivery catheter comprising a proximal end and a distal end, wherein the first delivery catheter is operably coupled to the feed catheter, wherein the first delivery catheter comprises a first delivery lumen extending from the proximal end of the first delivery catheter to a first infusion location located distally from the proximal end of the first delivery catheter, wherein the first infusion location comprises an opening through which fluid moving distally through the first delivery lumen exits the first delivery catheter, wherein the first delivery lumen is in fluid communication with first fluid pathway; a second delivery catheter comprising a proximal end and a distal end, wherein the second delivery catheter is operably coupled to the feed catheter, wherein the second delivery catheter comprises a second delivery lumen extending from the proximal end of the second delivery catheter to a second infusion location located distally from the proximal end of the second delivery catheter, wherein the second infusion location comprises an opening through which fluid moving distally through the second delivery lumen exits the second delivery catheter, wherein the second delivery lumen is in fluid communication with second fluid pathway; and a flow restrictor element operably attached to the feed catheter, wherein the flow restrictor element comprises a first capillary tube extending into the first fluid pathway of the feed catheter and a second capillary tube extending into the second fluid pathway of the feed catheter, wherein fluid flowing through the first fluid pathway of the feed catheter must pass through the first capillary tube before reaching the first delivery catheter, and wherein fluid flowing through the second fluid pathway of the feed catheter must pass through the second capillary tube before reaching the second delivery catheter.

In some embodiments of the fifth aspect of the infusion catheter systems described herein, the first capillary tube and the second capillary tube comprise flow-matched capillary tubes.

In another aspect, some embodiments of the infusion catheter systems described herein include a delivery catheter comprising a proximal end and a distal end, wherein the delivery catheter comprises an elongate body extending from the proximal end to the distal end; a first fluid pathway extending from the proximal end of the delivery catheter to a first infusion location located distally from the proximal end, wherein the first infusion location comprises an opening through which fluid moving distally through the first fluid pathway exits the delivery catheter; a second fluid pathway extending from a proximal end of the delivery catheter to a second infusion location located distally from the proximal end, wherein the second infusion location comprises an opening through which fluid moving distally through the second fluid pathway exits the delivery catheter, wherein the first fluid pathway and the second fluid pathway are separate and distinct from each other; a supply catheter comprising a proximal end and a distal end, wherein a supply lumen extends from the proximal end of the supply catheter to the distal end of the supply catheter; a flow restrictor element operably attaching the supply catheter and the delivery catheter, wherein the flow restrictor element comprises a first capillary tube extending into the first fluid pathway of the delivery catheter and a second capillary tube extending into the second fluid pathway of the delivery catheter, wherein fluid flowing from the supply lumen into the first fluid pathway must pass through the first capillary tube and wherein fluid flowing from the supply lumen into the second fluid pathway must pass through the second capillary tube; and a burr hole anchor comprising an anchor body operable to secure to bone surrounding a burr hole, wherein the anchor body comprises engagement surfaces configured to receive and immobilize the delivery catheter passing through the burr hole.

In another aspect, some embodiments of the infusion catheter systems described herein include a delivery catheter comprising a proximal end and a distal end, wherein the delivery catheter comprises an elongate body extending from the proximal end to the distal end; a first fluid pathway extending from the proximal end of the delivery catheter to a first infusion location located distally from the proximal end, wherein the first infusion location comprises an opening through which fluid moving distally through the first fluid pathway exits the delivery catheter; a second fluid pathway extending from a proximal end of the delivery catheter to a second infusion location located distally from the proximal end, wherein the second infusion location comprises an opening through which fluid moving distally through the second fluid pathway exits the delivery catheter, wherein the first fluid pathway and the second fluid pathway are separate and distinct from each other; a supply catheter comprising a proximal end and a distal end, wherein a supply lumen extends from the proximal end of the supply catheter to the distal end of the supply catheter; a flow restrictor element operably attaching the supply catheter and the delivery catheter, wherein the flow restrictor element comprises a first capillary tube extending into the first fluid pathway of the delivery catheter and a second capillary tube extending into the second fluid pathway of the delivery catheter, wherein fluid flowing from the supply lumen into the first fluid pathway must pass through the first capillary tube and wherein fluid flowing from the supply lumen into the second fluid pathway must pass through the second capillary tube; and a burr hole anchor comprising an anchor body operable to secure to bone surrounding a burr hole, wherein the anchor body comprises engagement surfaces configured to receive and immobilize the delivery catheter passing through the burr hole.

The words "preferred" and "preferably" refer to embodiments of the catheter systems and components that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The above summary is not intended to describe each embodiment or every implementation of the catheter systems described herein. Rather, a more complete understanding of the invention will become apparent and appreciated by reference to the following Description of Exemplary Embodiments and claims in view of the accompanying figures of the drawing.

BRIEF DESCRIPTION OF THE VIEWS OF THE DRAWING

The systems and methods will be further described with reference to the views of the drawing.

FIG. 1 is a side view of one illustrative embodiment of an infusion catheter system as described herein.

FIG. 2 is an exploded, side view of the catheter system of FIG. 1.

Figure 3:
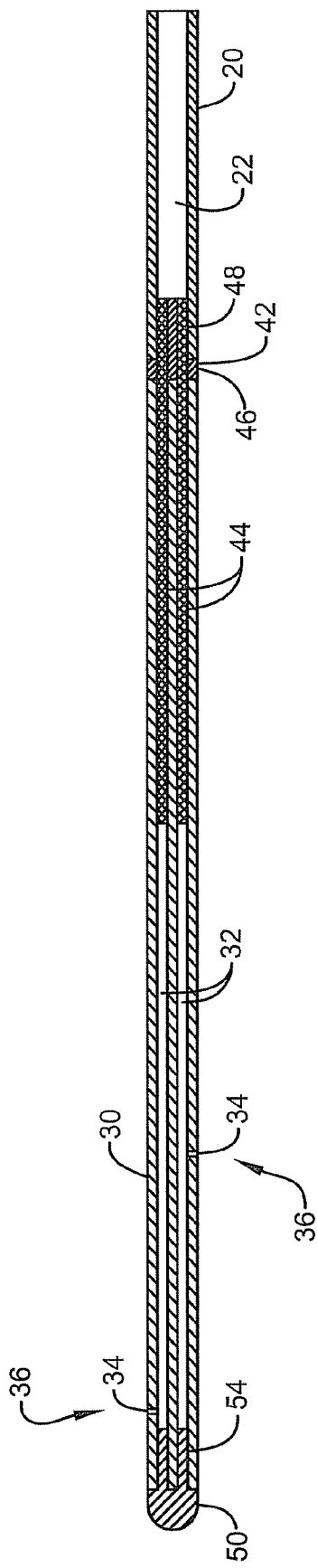
FIG. 3 is a side, cross-sectional view of the catheter system of FIG. 1.

The figures are rendered primarily for clarity and, as a result, are not necessarily drawn to scale.

DESCRIPTION OF ILLUSTRATIVE EMBODIMENTS

In the following detailed description of illustrative embodiments of the systems and methods described herein, reference is made to the accompanying figures of the drawing which form a part hereof, and in which are shown, by way of illustration, specific embodiments in which the systems and methods described herein may be practiced. It is to be understood that other embodiments may be utilized and structural changes may be made without departing from the scope of the present invention.

The fluids delivered using the systems and methods described herein preferably contain one or more drugs. A drug, as used herein, may include a therapeutic substance. Other substances may or may not be intended to have a therapeutic effect and are not easily classified, such as, e.g., saline solution, fluoroscopy agents, disease diagnostic agents, etc. Unless otherwise noted in the following paragraphs, the term "drug" as used herein may include any therapeutic, diagnostic, or other substance that is delivered using the implantable systems and methods described herein.

Therapeutic substances delivered using the systems and methods described herein may preferably be intended to have a therapeutic effect such as pharmaceutical compositions, genetic materials, biologics, and other substances. Pharmaceutical compositions are typically chemical foimulations intended to have a therapeutic effect such as intrathecal antispasmodics, pain medications, chemotherapeutic agents, and the like. Pharmaceutical compositions may be configured to function in an implanted environment with characteristics such as stability at body temperature to retain therapeutic qualities, concentration to reduce the frequency of replenishment, and the like. Genetic materials include substances intended to have a direct or indirect genetic therapeutic effect such as genetic vectors, genetic regulator elements, genetic structural elements, DNA, and the like. Biologics include substances that are living matter or derived from living matter intended to have a therapeutic effect such as stem cells, platelets, hormones, biologically produced chemicals, and the like.

As used herein and in the appended claims, the singular forms "a," "and," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term's "comprises" and variations thereof do not have a limiting meaning where these terms appear in the accompanying description. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

As used herein, the term "flow restrictor" refers to a resistance that is added to a system to bring the total resistance above a specified value; it does not necessarily refer to a singular component. For example, two "flow restrictors" (i.e. two components) of equal resistance placed in series at the tip of a given catheter could be functionally equivalent to a single flow restrictor whose resistance is twice that of either of the series restrictors taken by itself.

Although the flow restrictors may be used in an attempt to equalize flow rates through the different legs of a branched catheter system, the flow restrictors of the present invention may, in some instances, alternatively provide different flow rates through the different legs by varying the flow restriction provided by the different flow restrictors.

One potential benefit of flow restrictors as used in connection with the systems and methods described herein may be realized with catheter systems that, e.g., deliver a substance to two or more separate target areas within a body. Catheter systems may divide flow from a first or proximal catheter to two or more legs to which are coupled secondary or distal catheters, e.g., utilizing a "Y" coupling for a bifurcating catheter system. As a result, a single infusion pump may be used to deliver one or more drugs to multiple locations within a body. To provide substantially equal flow to each distal catheter, embodiments of the branching catheter systems may provide a flow resistor limiting flow through each leg. The flow restrictor may preferably contribute to balancing flow through each leg.

FIGS. 1-4 are different views of one exemplary catheter system 10 used to distribute fluids to locations within a body, e.g., separate areas of the brain. The catheter system 10 depicted in FIGS. 1-4 may include a supply tube 20 coupled to a delivery catheter 30 by a flow restrictor element 40 that is located between the supply tube 20 and the delivery catheter 30, with the components being arranged along a longitudinal axis 15. The catheter system 10 depicted in connection with FIGS. 1-4 is one example of a system in which flow is balanced through multiple lumens in the same delivery catheter, with each lumen including a separate exit opening to deliver fluid to a selected target site.

For simplicity, the tubes/catheters (e.g., supply tube 20/delivery catheter 30), flow restrictor elements (e.g., element 40), capillary tubes (e.g., capillary tubes 44), fluid pathways (e.g., fluid pathways 32), etc. are described herein as being generally cylindrical in shape. However, this configuration is not limiting, and embodiments having different shapes are certainly possible without departing from the scope of the invention. For example, the catheters and flow restrictor elements may include cross-sectional profiles that are triangular, oval, elliptical, hexagonal, semicircular, etc. Further, the term "diameter" may refer to the greatest cross-sectional dimension taken perpendicular to a longitudinal axis of the component, whether it has a circular or non-circular cross-sectional shape.

The supply tube 20 may define a supply lumen 22 that extends from a proximal end to a distal end. The supply tube 20 may be formed of any medically acceptable material, such as ETR silicone, polyurethane, polyurethane/silicone blends or other elastomers, etc. Although the supply tube 20 may be flexible, in some embodiments it may be provided in the form of a rigid tube manufactured from any suitable material or materials (e.g., metals, polymers, etc.). Also, the supply tube 20 may have a varying length and/or width depending on the application. For example, the supply tube 20 may be two or more times the length of the delivery catheter 30.

The proximal end of the supply tube 20 may be coupled to the flow restrictor element 40 as further described herein. Although not shown, the distal end of the supply tube 20 may be connected to a pump. While not wishing to be bound to any particular configuration, the pump may be, e.g., a SYNCHROMED II manufactured by Medtronic, Inc., of Fridley, Minn., USA.

The delivery catheter 30 may define multiple fluid pathways 32 that extend from the proximal end to the distal end. The delivery catheter 30 may be formed of any medically acceptable material, such as ETR silicone, polyurethane, polyurethane/silicone blends or other elastomers, etc. Although the delivery catheter 30 may be flexible, in some embodiments it may be provided in the form of a rigid tube manufactured from any suitable material or materials (e.g., metals, polymers, etc.). Also, the delivery catheter 30 may have a varying length (e.g., for a larger patient) and/or width depending on the application. In the embodiment depicted in FIGS. 1-4, the delivery catheter 30 includes four fluid pathways 32, with each of the fluid pathways 32 being provided as a separate and distinct lumen in the catheter 30. However, in alternative embodiments, the delivery catheter may include more or fewer fluid pathways without departing from the scope of the invention. For example, the delivery catheter 30 may have two, three, five, or more fluid pathways.

Each fluid pathway 32 includes an exit opening 34 located at an infusion section 36 along the length of the delivery catheter 30. When the delivery catheter 30 is inserted into a body, each infusion section 36 may correspond to a specific location within the body where fluid is to be dispersed.

The exit openings 34 may be circular, triangular, oval, elliptical, hexagonal, semicircular, etc. Further, each exit openings 34 may have the same diameter or a different diameter. The exit openings 34 may be formed by laser ablation, molding, drilling, machining, etc.

The distal end of the delivery catheter 30 may be coupled to a cap 50, which may substantially block the distal ends of the fluid pathways 32 to, e.g., seal the fluid pathways 32. The cap 50 may be attached to the delivery catheter 30 by an adhesive, melt bonding, welding, interference fit, etc. Further, in alternative embodiments, the cap 50 may be integral with the delivery catheter 30. The cap 50 may be formed of any medically acceptable material or materials.

The forward or distal end of the cap 50 depicted in FIGS. 1-3 is rounded. However, in alternative embodiments, the forward end of the cap 50 may be flat, conical, pyramidal, etc. The largest diameter of the cap 50 may be the same diameter of the delivery catheter 30. In alternative embodiments, the largest diameter of the cap 50 may be larger or smaller than the diameter of the delivery catheter 30.

The rear end of the cap 50 may include a plug portion 52 including individual plugs 54 for each of the fluid passageways 32. Each plug 54 may be sized relative to its corresponding fluid passageway 32 to provide an interference fit and to substantially block, e.g., seal, the fluid passageway 32 when attached. In some embodiments, the plugs 54 may be tapered, or may have any other suitable shape. The rear end of the cap 50 may be constructed of any suitable material or materials, e.g., rigid materials such as metals (e.g., stainless steel, titanium, tantalum, platinum/iridium), etc.

As used herein, the phrase "interference fit" refers to the coupling of a male member having a dimension larger than an undeflected or undeformed dimension of a mating female receptacle such that one or both of the male and female members deforms during assembly. As a result, a substantially tight and leak-free fit under all anticipated flow rates and pressures may be obtained once the parts are assembled.

The proximal end of the delivery catheter 30 may be coupled to the flow restrictor element 40 as further described herein. In this embodiment, the flow restrictor element 40 (see FIGS. 2-4) includes an element body 42 and multiple capillary tubes 44. It may be preferred that the capillary tubes 44 be located within the same region of the delivery catheter 30 such that the capillary tubes 44 are substantially coextensive with each other (although the capillary tubes 44 may have different lengths).

The flow restrictor element body 42 may be made from any medically acceptable material or materials. Examples of some potentially suitable materials may include, e.g., ETR silicone, polyurethane, polyurethane/silicone blends or other elastomers, etc. Examples of some potentially suitable materials may include, e.g., ELASTHANE 80A, Nu-Sil MED 4870 LSR, 65-75 Shore A durometer, etc.

The element body 42 may include an enlarged portion 46 that has a diameter that may be the same or larger than the diameter of the supply lumen 22 and/or the delivery catheter 30. The enlarged portion 46 may be operable to abut the supply tube 20 on one side and abut the delivery catheter 30 on the opposite side when the flow restrictor element 40 is coupled to the each of the catheters 20, 30.

The element body 42 may define one or more capillary apertures 48, each capillary aperture 48 sized to receive a capillary tube 44. The one or more capillary apertures 48 and capillary tubes 44 may align with the fluid passageways 34 of the delivery catheter 30. As such, each fluid passageway 34 may receive a capillary tube 44.

The capillary tubes 44 may by coupled within the capillary apertures 48 of the element body 42 and/or the lumens in the catheter 30 by any suitable technique, e.g., using adhesive, melt bonding, welding, interference fit, etc. One potential technique may include, e.g., slip-fitting a capillary tube 44 into an oversized capillary aperture 48 in the element body 42 and/or lumen/fluid passageway 34 of the catheter 30, following by re-flowing one or more of the components to fix the capillary tube 44 in position and force fluid to pass through the capillary tube 44, rather than around the capillary tube 44.

The capillary tubes 44 may be formed of any medically acceptable material, such as ETR silicone, polyurethane, polyurethane/silicone blends or other elastomers, glasses (e.g., fused silica, etc.), metals, etc. In at least one embodiment, the capillary tubes 44 may be fused silica capillary restrictors that have a length of about 4 inches (102 millimeters) and an inside diameter of about 0.0012 inches (30 microns).

The capillary tubes 44 may have a length such that they extend through the element body 42 and a portion of the delivery catheter 30. In FIG. 3, the capillary tubes 44 extend into the delivery catheter 30 about half the length of the delivery catheter 30. However, in other embodiments, the capillary tubes 44 may be longer or shorter relative to the delivery catheter 30 than shown in FIG. 4. For example, the capillary tubes may extend through the entire length of the delivery catheter 30 to the plugs 52 of the cap 50, or the capillary tubes 44 may only extend into a small portion of the delivery catheter 30. In at least one embodiment, the capillary tubes 44 may have a length of about 0.5 inches (13 millimeters) to about 1.5 inches (38 millimeters).

The capillary tubes 44 function as flow restrictors, e.g., the capillary tubes 44 provide flow resistance, and thus backpressure, so that a pressure sensor located upstream, e.g., in an infusion pump, can be utilized to detect cuts or occlusions between the capillary tube and the pump. That is, by creating a measurable pressure in lumen 22 of the supply tube 20 upstream of the capillary tubes 44, variations in that backpressure may potentially be utilized to predict occlusions (increased pressure) or leaks (decreased pressure).

The length and inner diameters of the capillary tubes 44 may be selected to obtain desired flow characteristics. For example, the cross-sectional openings within the capillary tubes 44 and their lengths may be selected to obtain desired flow characteristics based on, e.g., flow rates, fluid viscosity, the materials of the capillary tubes, etc.

Because the back pressure created by the capillary tubes 44 is sensitive to tolerance variations in the capillary tube construction, the capillary tubes 44 used in any one catheter system may be flow matched, i.e., each capillary tube 44 may have the same flow characteristics (e.g., each capillary tube may have the same flow rate at a given pressure for the same fluid). The flow matching may result in the use of capillary tubes 44 within the same catheter system that have different lengths, provided that the flow restrictions provided by the different capillary tubes 44 have the same flow characteristics.

Figure 5:
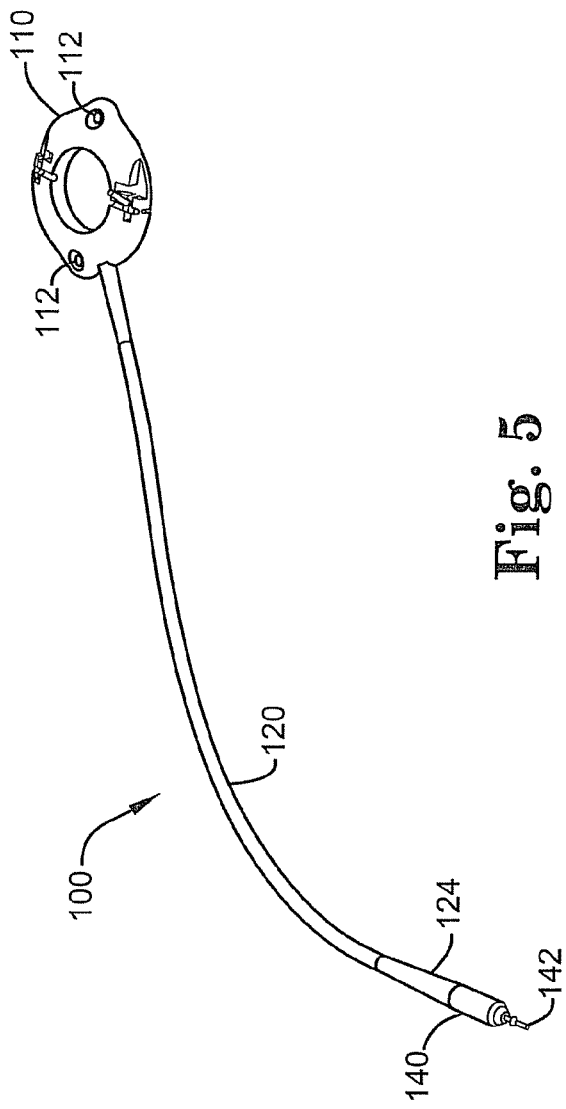
FIG. 5 is a system view of another illustrative embodiment of an infusion catheter system as described herein.
Figure 6:
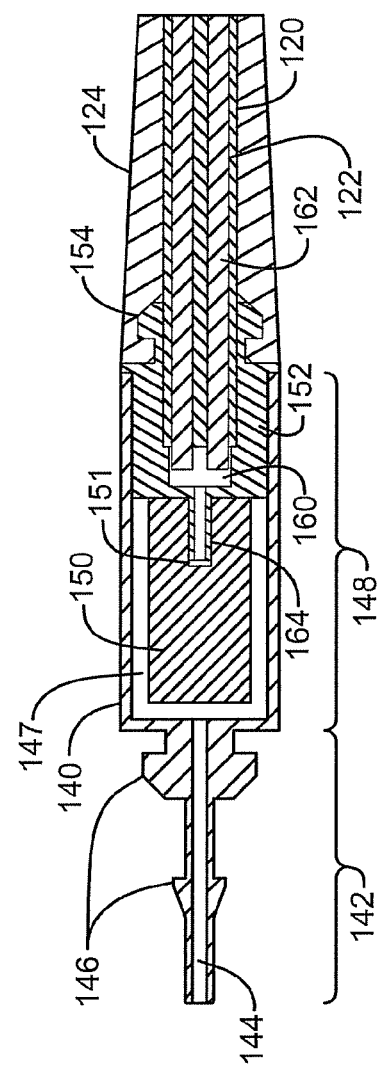
FIG. 6 is a side, cross-sectional view of the filter element of the catheter system of FIG. 5.
Figure 7:
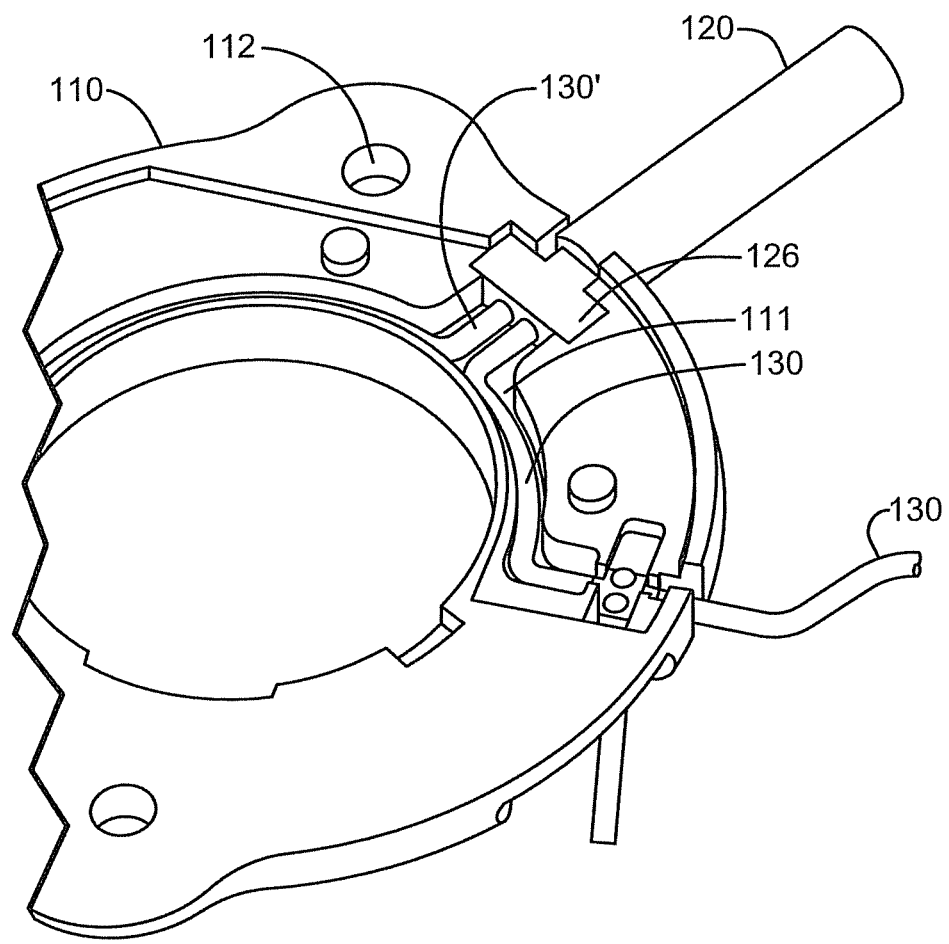
FIG. 7 is a bottom, perspective view of a portion of the anchor of the catheter system of FIG. 5.

FIGS. 5-7 are different views of another exemplary catheter system 100 in accordance with one embodiment of the invention that may be used to distribute fluids to locations within a body, e.g., separate areas of the brain. This exemplary catheter system embodiment is one in which the flow through the different delivery catheters is balanced by flow restrictors located in the fluid pathways.

The system 100 may include a filter element 140, a feed catheter 120, an anchor 110, and delivery catheters 130, 130'. Although not depicted as a part of the catheter system described with respect to FIGS. 1-4, it may be preferred to include a filter element upstream of the flow restrictors in any catheter system of the present invention to reduce the likelihood that particles may occlude flow through the flow restrictor and/or change the flow restriction provided by the flow restrictor (by, e.g., partially blocking the flow restrictor).

The filter element 140 may include a pin portion 142 for connecting to a device, e.g., a pump, implanted in an abdominal region of a patient. The pin portion 142 may include ramped flanges 146 to further secure the filter element 140 to the fluid apparatus. The filter element 140 may define a bore 144 through the pin portion 142 and into the filter portion 148.

The feed catheter 120 may extend to an anchor 110, which, e.g., may be attached to the skull of a patient. The anchor 110 may then couple the feed catheter 120 to the delivery catheters 130, 130', each of which, e.g., may be inserted into a specific region of the patient for fluid delivery to those specific regions.

Although the embodiment depicted in FIGS. 5-7 includes a bifurcating catheter system 100, the present invention may include catheter systems with three or more branches. In other variations, although the depicted system is implanted for delivery into the brain of a patient, it should be understood that catheter systems of the present invention may be used to deliver fluids to other areas of the body.

A filter 150 may preferably be attached to, or integrally formed with, the filter element 140. In one embodiment, the filter element 140 may preferably be made from titanium with the filter 150 being a sintered titanium member welded to the element 140. However, other embodiments in which the filter 150 is a separate component, e.g., fits within the filter element, or embodiments wherein one or both of the filter 150 and the filter element 140 are made from other biocompatible materials, e.g., polysulfone, polycarbonate, ethylene tetrafluoroethylene (ETFE), etc., may also be used without departing from the scope of the invention. In some embodiments, paper and/or fiber-type filters may also be used.

The filter portion 148 of the filter element 140 may include a larger bore that surrounds the filter 150 and part of the flow restrictor element 152. In this embodiment, the filter portion 148 may include a gap 147 (see FIG. 6) so that the interior of the bore of the filter portion 148 may not completely abut the filter 150.

The gap 147 between the element 140 and the filter 150 may provide increased surface area (and, thus, potentially increased filtering capacity) over which to filter the passing fluid. To further improve fluid passage through the filter 150, it may be preferable that surface of the filter 150 includes curvature, e.g., a cup-shaped curvature. However, such a configuration is not required. In fact, filters of most any configuration are possible without departing from the scope of the invention. Further, in this embodiment, the filter 150 may define a bore 151 for receiving a pin portion 164 of the flow restrictor element 152.

The micron rating of the filter 150 may preferably be selected to reduce the likelihood that downstream flow restrictors used to control fluid flow through the branches will occlude with debris. In one exemplary embodiment, the filter 150 may have a micron rating of about 5 microns.

It may be preferred that the filter or filters be positioned upstream of any point at which fluid flow is divided for delivery into the different branches of any branched catheter system. In the depicted embodiment, the location of the filter 150 may be beneficial to ensure that occlusion of the filter pores has an essentially equivalent effect on flow to all branches (i.e., both capillary tubes 162). However, other configurations that replace the filter 150 with branch filters or, alternatively, utilize staged filters are contemplated.

The diameter of the flow restrictor element 152 may be sized slightly larger than the bore of the filter portion 148 of the filter element 140 such that the flow restrictor element 152 may fit within the filter element 140 with an interference fit. Alternatively, the flow restrictor element 152 may be coupled within the element 152 by any suitable combination of adhesive, melt bonding, welding (e.g., 360 degree welds), reflowing, etc.

The flow restrictor element 152 may define a bore sized so that the feed catheter 120 may fit within the bore of the flow restrictor element 152 with an interference fit. Alternatively, the feed catheter 120 may by coupled within the flow restrictor element 152 by any suitable combination of adhesive, melt bonding, welding, reflowing, etc. A portion 160 of flow restrictor element 152 may be substantially similar to the flow restrictor element 40 as described herein with reference to FIGS. 1-4. The bore of the flow restrictor element 152 may further define an aperture that corresponds with the bore 151 of the filter 150 for receiving a pin portion 164 of the flow restrictor element 152. The flow restrictor element 152 may further define flanges 154 for engaging the strain relief sleeve 124 as described herein.

In at least one embodiment, the portion 160 of the flow restrictor element 152 may not be a unitary part of the flow restrictor element 152, i.e., they may be separate pieces.

Figure 4:
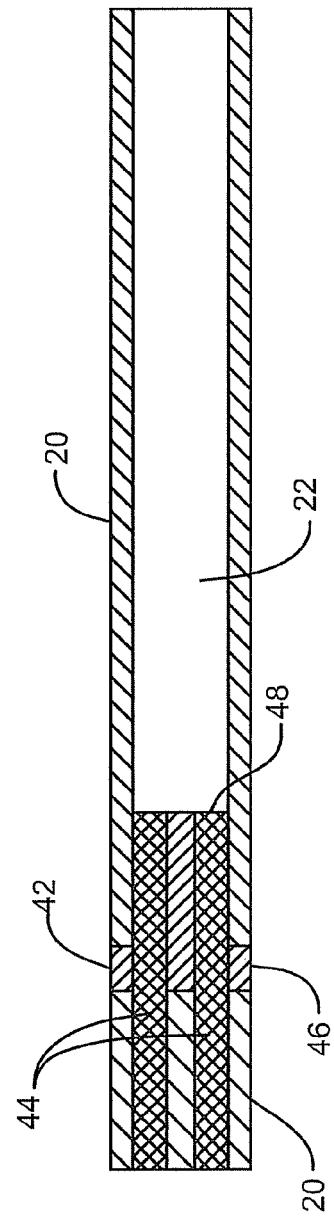
FIG. 4 is a partial, cross-sectional view of the catheter system of FIG. 1.

The catheter system 100 preferably includes capillary tubes 162 that fit within apertures in the portion 160 similar to the capillary apertures 48 described herein in FIGS. 2-4. The capillary tubes 162 preferably function as flow restrictors similar to the capillary tubes 44 as described herein. In at least one embodiment, the capillary tubes 162 may be fused silica capillary restrictors that have a length of about 4 inches (102 millimeters) and an inside diameter of about 0.0012 inches (30 microns).

The capillary tubes 162 are preferably located within fluid pathways (lumens) 122 of the feed catheter 120. In the depicted embodiment, it may be preferred that the capillary tubes 162 extend from the proximal end of the feed catheter 120 to the distal end of the feed catheter 120 (i.e., proximate the anchor 110). It may further be preferred that each of the capillary tubes 162 be directly connected to the one of the delivery catheters 130 at the distal ends of the capillary tubes 162. In one manner, the capillary tubes 162 may be described as being located within the same region of the feed catheter 120 such that the capillary tubes 162 are substantially coextensive with each other The proximal end of the feed catheter 120 may fit within the bore of the flow restrictor element 152 and abut the portion 160 of the flow restrictor element 152. The capillary tubes 162 of the flow restrictor element 152 may extend into the fluid passageways 122 of the feed catheter 120.

The capillary tubes 162 may by coupled within the portion 160 of the element 152 and/or the lumens in the feed catheter 120 by any suitable technique, e.g., using adhesive, melt bonding, welding, interference fit, etc. One potential technique may include, e.g., slip-fitting a capillary tube 162 into an oversized lumen/fluid passageway 122 of the catheter 120, following by re-flowing one or more of the components to fix the capillary tubes 162 in position and force fluid to pass through the capillary tubes 162 (rather than around the capillary tubes 162).

The feed catheter 120 may further include a strain relief sleeve 124 that may extend over a portion of the flow restrictor element 152 and a portion of the feed catheter 120 to, e.g., provide further support to the feed catheter 120. The strain relief sleeve 124 may be tapered with its largest diameter surrounding the flow restrictor element 152 as shown. In this embodiment, the strain relief sleeve 124 and the feed catheter 120 may be separate pieces. In other embodiments, the strain relief sleeve 124 may be integral with the feed catheter 120.

As shown in FIG. 5, the feed catheter 120 may extend to an optional anchor 110. The anchor 110 may be for securing catheters relative to a body portal, e.g., securing delivery catheters 130, 130' (shown in FIG. 7) relative to burr holes (not shown) within which they may be inserted. As shown in FIG. 7, the feed catheter 120 may include a connector block 126 that cooperates with the anchor 110 to retain the feed catheter 120 in position relative to the anchor 110. The anchor 110 may include one or more troughs 111 through which delivery catheters 130, 130' extend before reaching the target sites to which fluid is to be delivered using the catheter system.

Although the catheter system 100 shown in FIGS. 5 & 7 utilizes anchor 110, no anchor may be used or any other type of anchor may be used with catheter system 100 as known by one having ordinary skill in the art. The anchor 110 may be secured to tissue, e.g., an outer surface of the skull of a patient, via any acceptable method, e.g., bone screws (not shown) extending through openings or screw holes 112 formed through the anchor 110.

Figure 8:
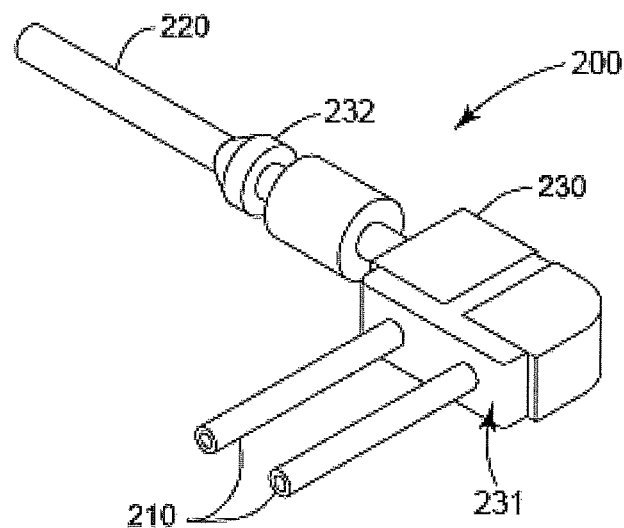
FIG. 8 is a perspective view of another illustrative embodiment of an infusion catheter system as described herein.
Figure 9:
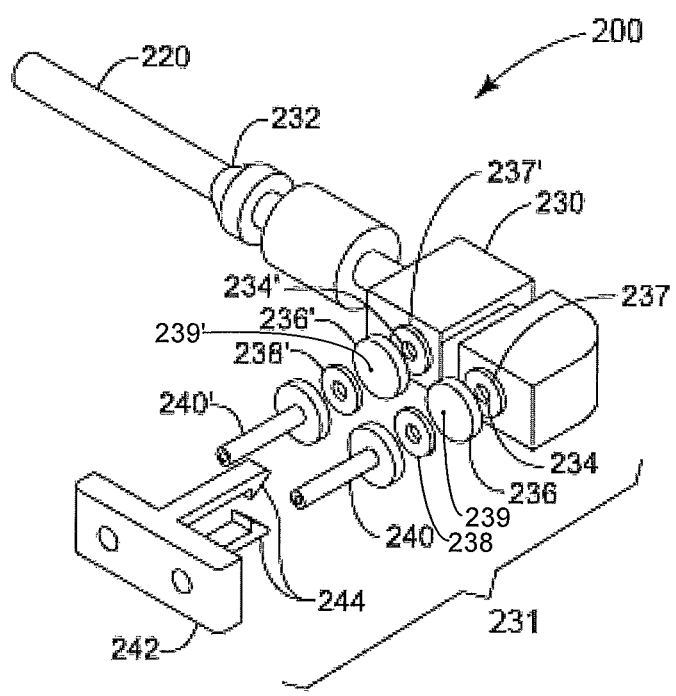
FIG. 9 is an exploded perspective view of the catheter system of FIG. 8.

FIGS. 8-9 depict another exemplary embodiment of another infusion catheter system 200 used to distribute fluids to locations within a body, e.g., separate areas of the brain. The system 200 may include a supply tube, delivery catheters 210, and a connector 230. Like the embodiment depicted in FIGS. 5-7, the catheter system of FIGS. 8 & 9 is one in which the flow through the different delivery catheters is balanced by flow restrictors located in the fluid pathways.

The supply tube may be similar to the supply tube 20 described herein with reference to FIGS. 1-4. The connector 230 may include a supply port 232, a first exit port 234, and second exit port 234'. The supply port 232 may be coupled to a supply tube (not shown) using a hollow fitting 220 that extends into the lumen of the supply tube. The supply tube may by coupled to the fitting 220 of the supply port 232 using any technique that provides a fluid-tight connection, e.g., adhesives, melt bonding, welding, reflowing, etc. In at least one embodiment, the connector 230 may be embedded into a cranial anchor, e.g., the anchor 110 show in FIG. 5 or the anchors depicted in FIGS. 11-14.

The connector 230 may fluidly couple the supply tube 220 to each of the two delivery catheters 210. In other embodiments, the connector 230 may fluidly couple the supply tube to one delivery catheter (with the other pathway closed) or to three or more delivery catheters (by including three or more exit ports).

The catheter connection apparatus 231 may include catheter connection pins 240, 240', restrictors 236, 236', first gaskets 237, 237', second gaskets 238, 238', openings (orifices) 239, 239' and retaining clip 242. Although FIG. 9 shows two connections, the description herein will describe the catheter connection with relation to a single catheter connection. The second catheter connection may be substantially the same as the first catheter connection.

The first gasket 237 may be donut shaped and formed of any medically acceptable material, such as ETR silicone, polyurethane, polyurethane/silicone blends or other elastomers, etc. The first gasket 237 may abut the exit port 234 of the connector 230 on one side and abut the restrictor 236 on its other side so as to provide a seal between the exit port 234 and the restrictor 236.

The second gasket 238 may be substantially the same as the first gasket 237 and may abut restrictor 236 on one side and abut the catheter connection pin 240 on its other side so as to provide a seal between the restrictor 236 and the catheter connection pin 240.

The catheter connection pin 240 may define a bore and include an enlarged portion, which, e.g., may be about the same size as the first and second gaskets 237, 238 and/or the restrictor 236. The retaining clip 240 holds the catheter connection pin 240, first and second gaskets 237 238, and the restrictor 236 together to substantially seal the connection to the connector 230.

The retaining clip 240 may include a pair of arms 244 for securing the clip 240 to a receiving portion 246 of the connector through, e.g., a snap-fit. In other embodiments, the retaining clip 240 may utilize any different retention mechanism to secure the components to the connector 230 as would be known by one having ordinary skill in the art. Regardless of the specific mechanism, it may be preferred that the structure result in axial compression of the gaskets to provide fluid-tight connections between the various components.

The restrictor 236 may be, e.g., a disc-shaped, ruby body having about a 0.060 inch (1.5 millimeters) outside diameter, about a 0.010 inch thickness (240 microns), and about a 0.00029 inch (7 microns) diameter opening 239. It may be preferred that the opening 239 have a diameter of 7 microns to 10 microns, although smaller and/or larger openings may be used based on desired flow rates through the restrictor. While not wishing to be bound to any particular configuration, the flow restrictor 236 may be a ruby straight hole orifice manufactured by Bird Precision, Inc. of Waltham, Mass. USA. In other embodiments, the restrictor 236 may be a custom micro-hole element with an opening 239 made by any suitable technique, e.g., microdrilling, laser drilling, etc.

Restrictors may used to control (e.g., balance) flow through the delivery catheters. Further, multiple restrictors in a system may be flow-matched. Size, and/or shape of the opening of the restrictors may be selected to obtain desired flow in view of flow rates, fluid viscosity, etc. As discussed herein, one or more filters may be provided upstream of the flow restrictors 236.

The catheter connection pin 240 may include an enlarged section for abutting the second gasket 238 on one side and abutting the retainer clip 240 on the other side. The end of the connection pin 240 may extend through an aperture in the retainer clip 234 and may be coupled to a catheter, e.g., a deliver catheter 210.

The delivery catheters 210 may be attached the catheter connections pins 240, 240' by any technique as known by one having ordinary skill in the art.

Figure 10:
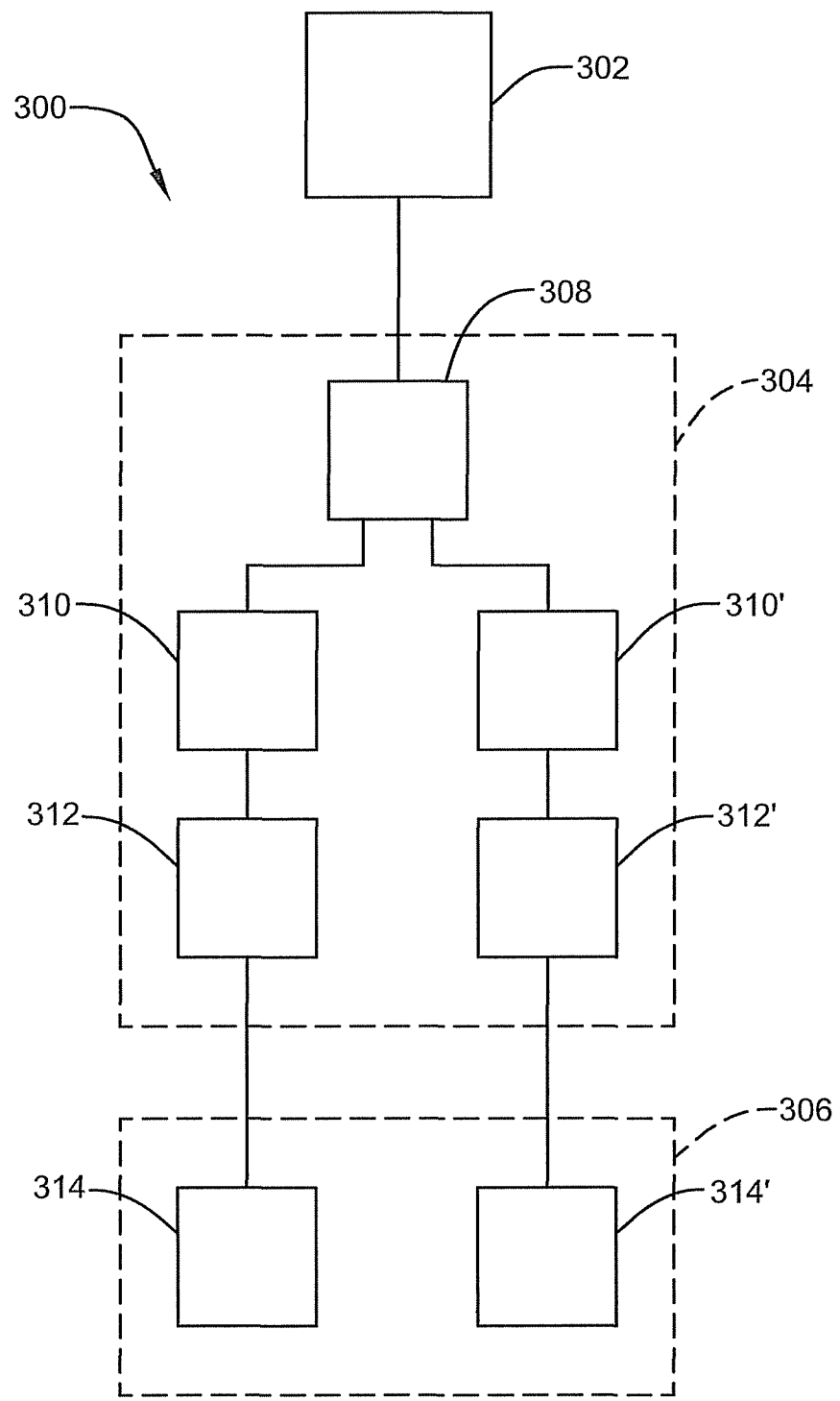
FIG. 10 is a diagrammatic view of another illustrative embodiment of an infusion catheter system as described herein.

FIG. 10 diagrammatically depicts another exemplary embodiment of an infusion catheter system 300 used to distribute fluids to locations within a body, e.g., separate areas of the brain. Although this FIG. 10 is diagrammatically represented, the parts described herein may be substantially similar to the part previously described. The system 300 may include supply tube 302, a delivery catheter 306, and a connector 304.

The connector 304 may include a supply port 308 for receiving fluid from the supply tube 302. In this embodiment, the fluid path bifurcates after being received by the supply port 308 into two paths. Each path directs the fluid through one of the restrictors 310, 310' and then through one of the exit ports 312, 312'. In at least one embodiment, the restrictors 310, 310' may be flow matched, i.e., each restrictor 310, 310' may have the same flow characteristics.

The delivery catheter 306 may include fluid pathways 314, 314'. The delivery catheter 306 may be coupled to the connector 304 such that each of the exit ports 312, 312' is in fluid communication with one of the fluid pathways 314, 314'.

An anchor assembly that may be used to secure delivery catheters of the catheter systems described herein with respect to a burr hole formed in a patient's skull are described in commonly-assigned U.S. patent application Ser. No. 12/357,120, entitled, "BURR HOLE ANCHORS, SYSTEMS AND METHODS", filed on Jan. 21, 2009, which application is hereby incorporated herein by reference in its entirety to the extent it does not conflict with the disclosure presented herein. The burr hole anchor assemblies described therein form part of a system for infusing a therapeutic agent into the patient's brain via an intraparenchymal (IPA) or intracerbroventricular (ICV) delivery catheter that passes through a burr hole formed in the skull. The catheter systems described in connection with the anchor assembly embodiments will include supply or feed catheters and delivery catheters each of which may be formed of any medically acceptable material, such as ETR silicone, polyurethane, polyurethane/silicone blends or other elastomers, etc. While the catheters may be flexible, in some embodiments all or a portion thereof may be provided in the form of a rigid tube manufactured from any suitable material or materials (e.g., metals, polymers, etc.).

Figure 11:
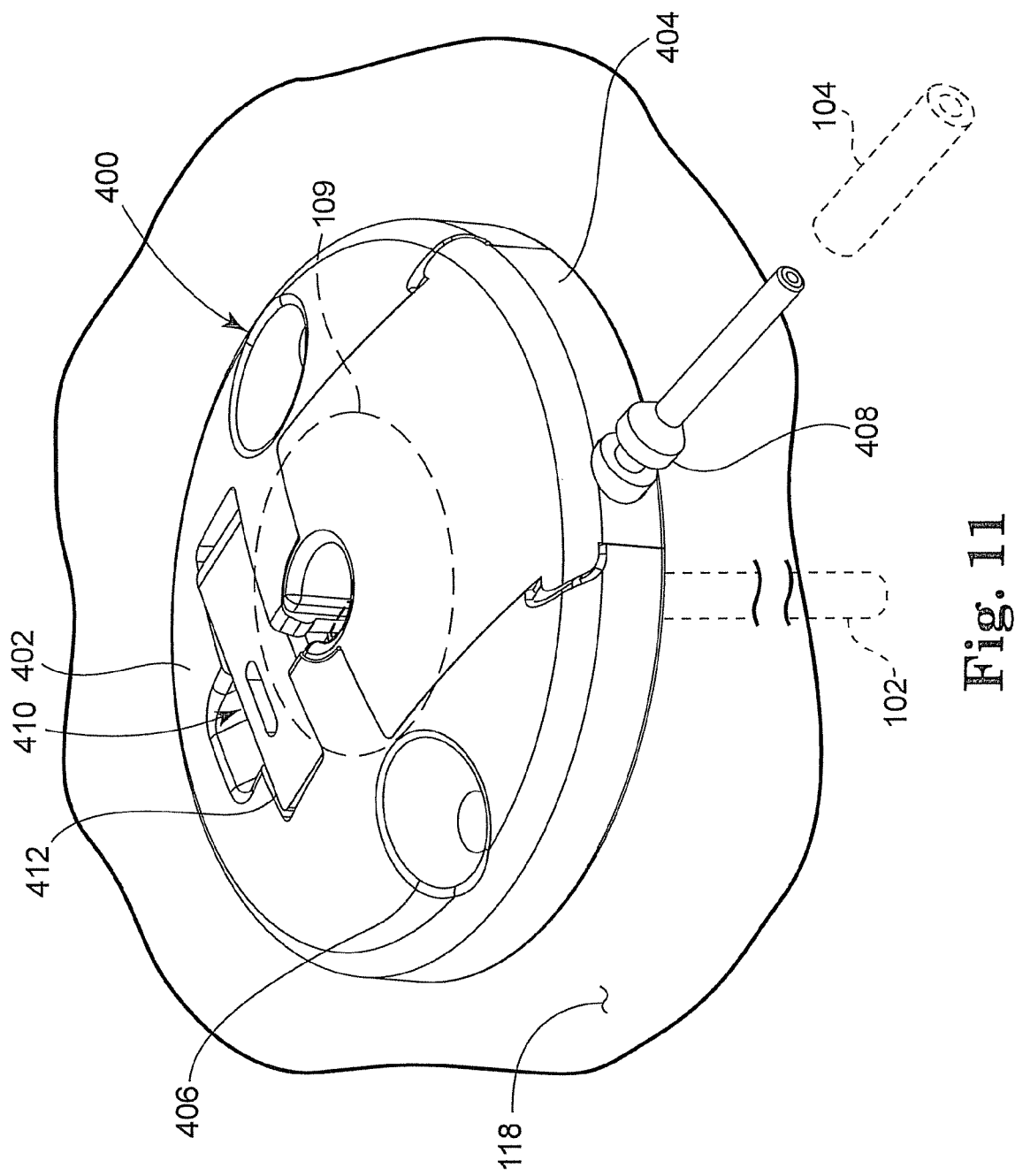
FIG. 11 is an enlarged perspective view of one embodiment of an anchor that may be used in some embodiments of the infusion catheter systems described herein.

FIG. 11 illustrates an enlarged perspective view of an anchor system that includes anchor or anchor assembly 400 useful with a catheter infusion system. The infusion system may include a delivery catheter 102 that may be implanted, e.g., within a mammalian brain through a burr hole 109 (located underneath the anchor 400). A second medical tube, e.g., a feed or supply catheter 104 may also be provided that is coupled to a therapy source or reservoir (e.g. an implantable or external pump, not shown). The delivery catheter 102 may, via the anchor 400, be operatively connected to an end of the supply catheter 104 via one or more connectors, embodiments of which are described below.

The anchor may include a base 402 and a module or insert 404 that together form a body of the anchor. The anchor 400 (e.g., the base 402) may be secured to selected tissue 118 at a selected location via any acceptable method (e.g., sutures, tissue anchors, bone screws, etc.). In the case of a burr hole anchor surrounding a burr hole on the outer surface of the skull, the anchor 400 may be secured using, e.g., bone screws (not shown) extending through openings 406 formed through the base 402. Although the anchor 400 may be designed for use as a burr hole anchor (where the anchor body is operable to be secured to bone tissue surrounding a burr hole in patient's skull), the anchors used in the systems described herein may include anchor body that is operable to be secured to selected tissue at any selected location on or in a patient. The selected tissue to which the anchor may be secured may include bone tissue, soft tissue, etc.

The body of the anchor 400 may further include a supply catheter feed pin 408 which, in one embodiment, extends outwardly from a peripheral edge of the anchor body, e.g., from the insert 404. The feed pin 408 may include a tubular male member that may be received within the lumen of the supply catheter 104.

The anchor 400 may further include a catheter cutting or shearing mechanism 410. In one embodiment, the mechanism 410 is formed, at least in part, by a door 412 pivotally attached to the body, e.g., the base, and having a shearing edge described in more detail in U.S. patent application Ser. No. 12/357,120, entitled, "BURR HOLE ANCHORS, SYSTEMS AND METHODS", filed on Jan. 21, 2009.

Figure 12:
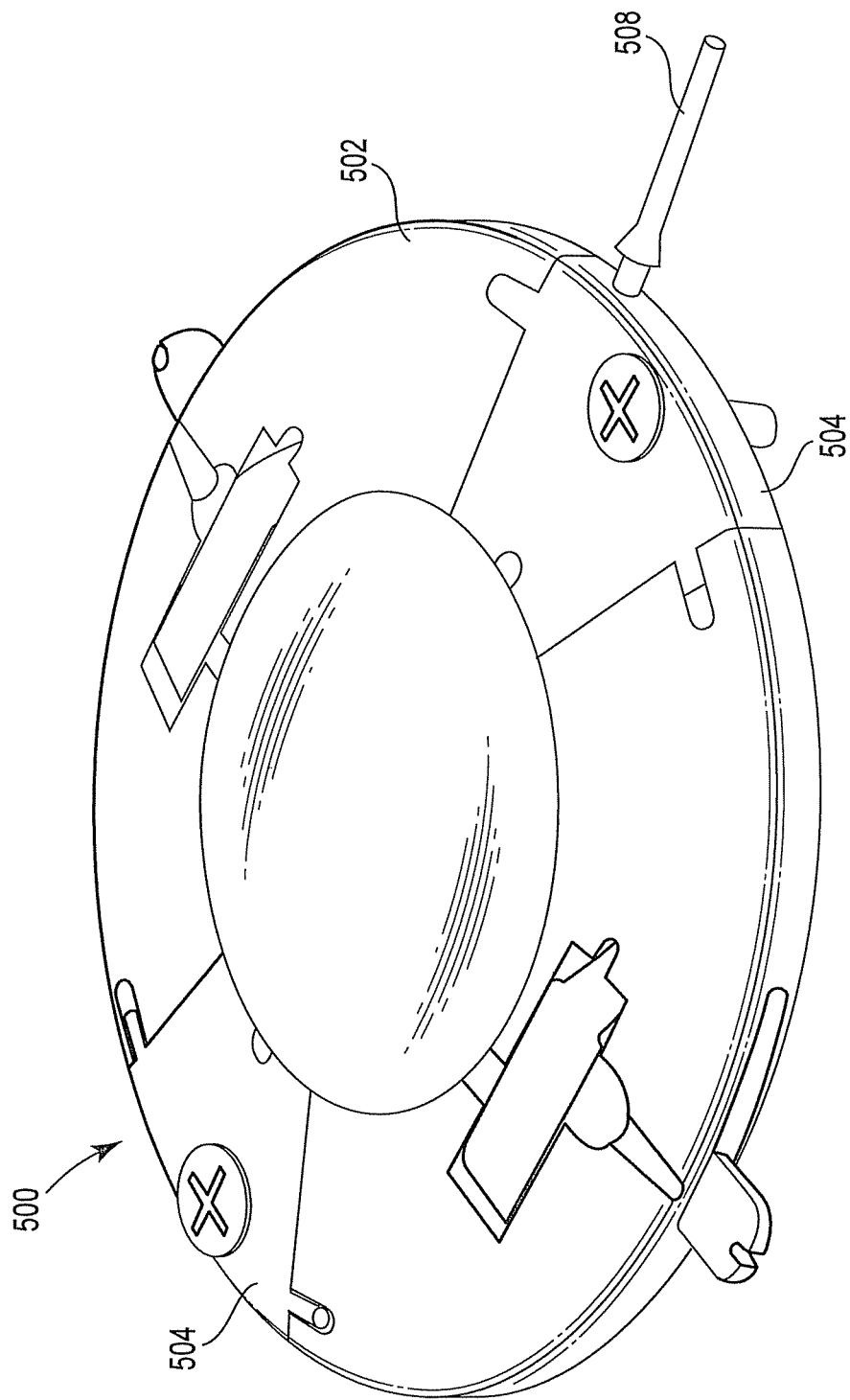
FIG. 12 is a top view of another embodiment of an anchor that may be used in some embodiments of the infusion catheter systems described herein.
Figure 13:
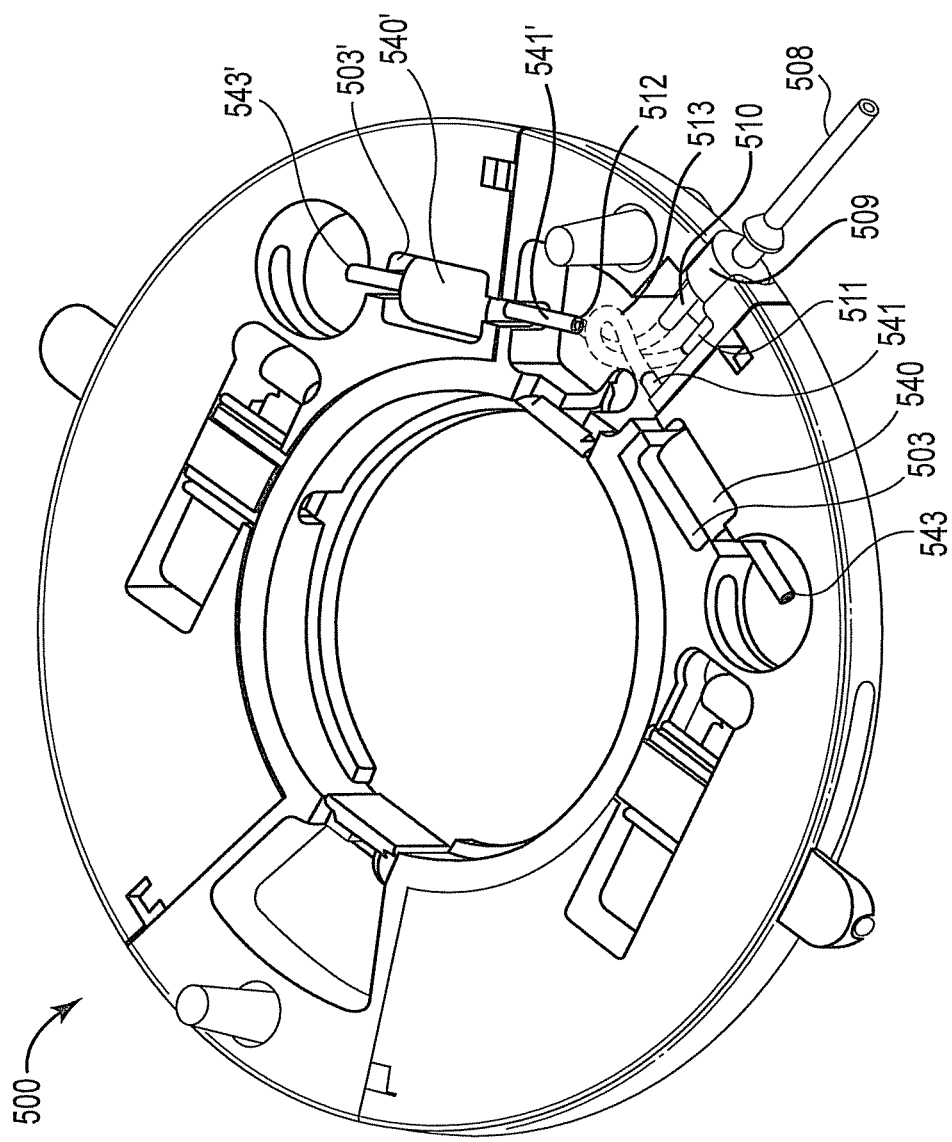
FIG. 13 is a bottom view of the anchor of FIG. 12 housing flow restrictors as described in connection with some embodiments of the infusion catheter systems described herein.

FIGS. 12 and 13 show another embodiment of an anchor 500 (e.g., a burr hole anchor) that may be used with the catheter systems described herein, wherein one or more flow restrictors may be housed in the anchor body 502. As described herein, some embodiments of the systems described herein may include flow restrictors positioned in the anchors used to secure the delivery catheters implanted in a patient and positioned to deliver fluids to a predetermined target site. In one embodiment, the anchor is attached to a patient's skull around a burr hole through which the delivery catheter was implanted. The flow restrictors in the anchors will be configured to be fluidly connected to a delivery catheter and fluidly connected to a supply catheter and to be positioned within the fluid path delivering fluid to the delivery catheter. Positioning the flow restrictors in the anchors may be advantageous because the flow restrictors may have a form factor that may be more amenable to placement in the anchors rather than in the delivery catheters. In addition, replacement of flow restrictors that may become clogged or otherwise impaired or replacement to adjust fluid flow rates into the various delivery catheters may be more easily accomplished by locating the flow restrictors in anchors that may be more easily accessed after initial deployment of the system in a patient.

FIGS. 12 and 13 are, respectively, top and bottom views of one embodiment of an anchor 500 that may be used in some embodiments of the catheter systems described herein. The anchor 500 may include a supply catheter pin 508 similar in many respects to the supply catheter pin 408 described above to connect a fluid source (e.g., pump or other source of therapeutic agent) to a supply catheter (not shown). In some embodiments, the anchor 500 may include one or more removable caps 504 that can be used to cover the outer or top surface of portions of the anchor body 502.

The anchor body 502 includes cavities 503 and 503' in which flow restrictors 540 and 541' are located. The cavities 503 and 503' may be open on the bottom surface of the anchor body 502 to allow for removal and replacement of the flow restrictors 540 and 540' in the anchor body 502. Although access to the flow restrictors 540 and 540' in the depicted embodiment is through openings in the bottom surface of the anchor body 502, the cavities 503 and 503' in the anchor body 502 may also or alternatively open on the top surface of the anchor body 502 (i.e., the surface depicted in FIG. 12), with the cavities covered by a cap 504. Anchor bodies with cavities that allow access to the flow restrictors located therein through the top surface of the anchor assembly to further facilitate their removal and replacement without requiring removal of the anchor body from its secured location.

The anchor body 502 may include a connector 509 that separates the flow into the anchor 500 into two streams, with a first stream flowing to the first flow restrictor 540 and a second stream flowing to the second flow restrictor 540'. The connector 509 includes a first exit port 510 connected to the inlet port 541 of the first flow restrictor 540 by tubing 513 and a second exit port 511 connected to the inlet port 541' of the second flow restrictor 540' by tubing 512. The other ports 543 and 543', respectively, of the first and second restrictors are in fluid connection with a first and second delivery catheter as described herein (not shown in FIG. 13).

Although a connector 509 in the form of a manifold that is separate and discrete from the anchor body 502 and tubes 512 and 513 is used to distribute flow in the depicted embodiment to the inlet ports of the flow restrictors located in the catheter body 502, other embodiments may use any other suitable connector to distribute the incoming fluid to two or more different fluid paths. The connectors used to distribute flow (from, e.g., supply tube, supply catheter, etc.) to two or more different fluid paths as described herein may be provided in any suitable form, e.g., a discrete manifold that includes one or more supply ports and two or more exit ports, a Y-fitting, a T-fitting, a cavity formed in an anchor body with the cavity including one or more supply ports and two or more exit ports, etc.

In some embodiments, the distribution of flow from the inlet 508 to the first and second delivery catheters (not shown in FIGS. 12 and 13) is controlled by the flow restrictors 540 and 540'. In some embodiments, the flow through the flow restrictors 540 and 540' may be substantially equal, while in other embodiments, the flow may be distributed unequally, but in a selected ration, e.g., 60% through one flow restrictor and 40% through the other flow restrictor, 75% through one flow restrictor and 25% through the other flow restrictor, etc.

Also, although the connector 509 and the flow restrictors 540 and 540' are, in the depicted embodiment, provided as separate and discrete articles, in some embodiments, two or more flow restrictors may be integrated into a connector assembly such as, e.g., the system 200 depicted in FIGS. 8 and 9. Such an integrated connector and flow restrictors may, in some embodiments, be located within an anchor as described herein to both distribute and control (e.g., balance) fluid flow from a single supply source to two or more delivery catheters.

Figure 14:
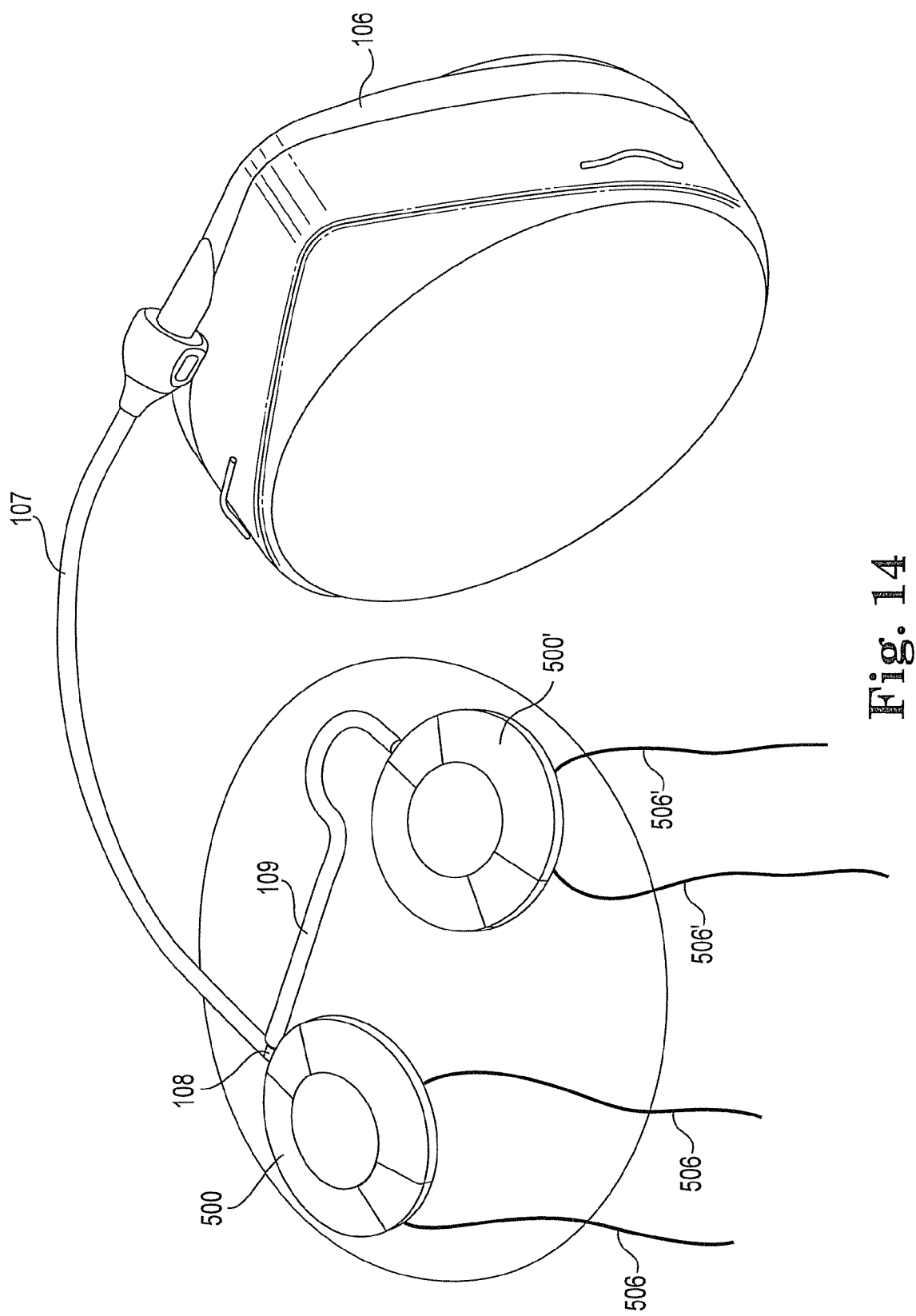
FIG. 14 is a diagrammatic view of one embodiment of an infusion catheter system as described herein, the system having therapy delivery devices (e.g., delivery catheters), two anchors all attached to a therapy source (e.g., an infusion pump) and a supply or feed device (e.g., supply catheters)

One embodiment of a catheter system including two anchors 500, 500' is depicted in FIG. 14. In the depicted embodiment, each of the anchors 500, 500' may be used to distribute flow from a single fluid source 106 (e.g., a pump or other source of therapeutic agent) to one or more delivery catheters 506 extending from the anchors 500, 500'. The flow from fluid source 106 to the anchors may be delivered by a supply tube 107 that directs flow into a supply port of connector 108 (e.g., a connector that, in this embodiment is in the form of a T-fitting), with a first portion of the fluid passing through the connector 108 to the anchor 500 through an exit port of the connector 108 and a second portion of the flow passing to the second anchor 500' through a supply tube 109 connected to another exit port of the connector 108.

The connector 509 may, as in the depicted embodiment, be attached to the anchor 500 while the supply tube 109 fluidly connects the second anchor 500' to the first anchor 500 to form a daisy-chain system of anchors 500, 500' that are fed from a single fluid source. Each of the anchors may be used to feed and connect one or more delivery catheters such that, in one multi-anchor embodiment, the system includes two anchors, with each anchor feeding one delivery catheter.

In the embodiment depicted in FIG. 14, the system includes two pairs of delivery catheters 506, with each pair of delivery catheters 506 being connected to the components in the anchors 500, 500' such that fluid from source 106 is distributed to the delivery catheters 506 in manner dictated by the flow restrictors deployed within the infusion catheter system. As discussed herein, in some embodiments, those flow restrictors may be advantageously located in the anchors 500, 500'. In some embodiments, one anchor, e.g., anchor 500 may preferably include two flow restrictors, each of which distributes flow to a separate delivery catheter 506 attached to the anchor 500 and the second anchor 500' may preferably include two flow restrictors, each of which distributes flow to a separate delivery catheter 506 attached to the anchor 500'.

Although the embodiment of an infusion catheter system depicted in FIG. 14 includes two anchors 500, 500' that are each connected to a separate pair of delivery catheters 506, other embodiments may include three or more anchors. In another variation, each of the anchors may be used to deliver fluid to any selected number of delivery catheters 506. For example, anchor 500' may be connected to only one delivery catheter 506 or three or more delivery catheters depending on the needs of a user.

By employing a separate flow restrictor located upstream of each of the delivery catheters, relative fluid flow into each of the delivery catheters 506 may be controlled. For example, if the flow restrictors used to feed each of the four delivery catheters 506 depicted in FIG. 14 are selected to provide substantially equivalent flow restrictions, then the fluid flow to each of the delivery catheters may be substantially equal (e.g., approximately 25% of the flow from the source 106 would be delivered to each of the delivery catheters 506—assuming that all other flow restrictions in each fluid path are equal and/or insignificant as compared to the flow restriction provided by the flow restrictors). Other distributions of fluid flow between the delivery catheters 506 may be achieved by selecting flow restrictors that provide different levels of flow restriction.

Each of the delivery catheters used in a system such as that depicted in FIG. 14 may include one or more delivery lumens that extend through the delivery catheters to one or more infusion locations along the delivery catheter. The delivery catheters may be funned of any medically acceptable material, such as ETR silicone, polyurethane, polyurethane/silicone blends or other elastomers, etc. Although the delivery catheters may be flexible, in some embodiments they may be provided in the form of a rigid tube manufactured from any suitable material or materials (e.g., metals, polymers, etc.).

Figure 15:
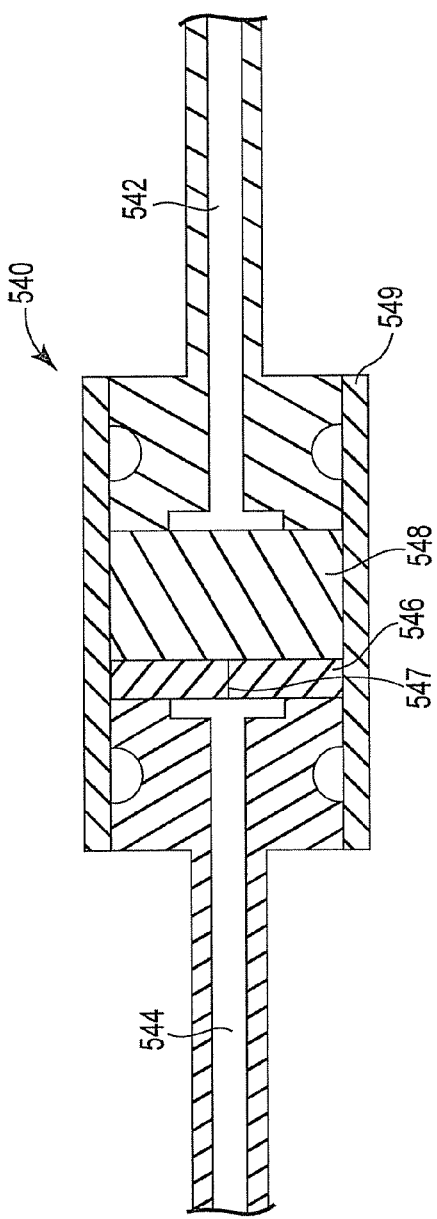
FIG. 15 is a cross-sectional view of one embodiment of a flow restrictor that may be housed in an anchor such as that shown in FIG. 13.
Figure 16:
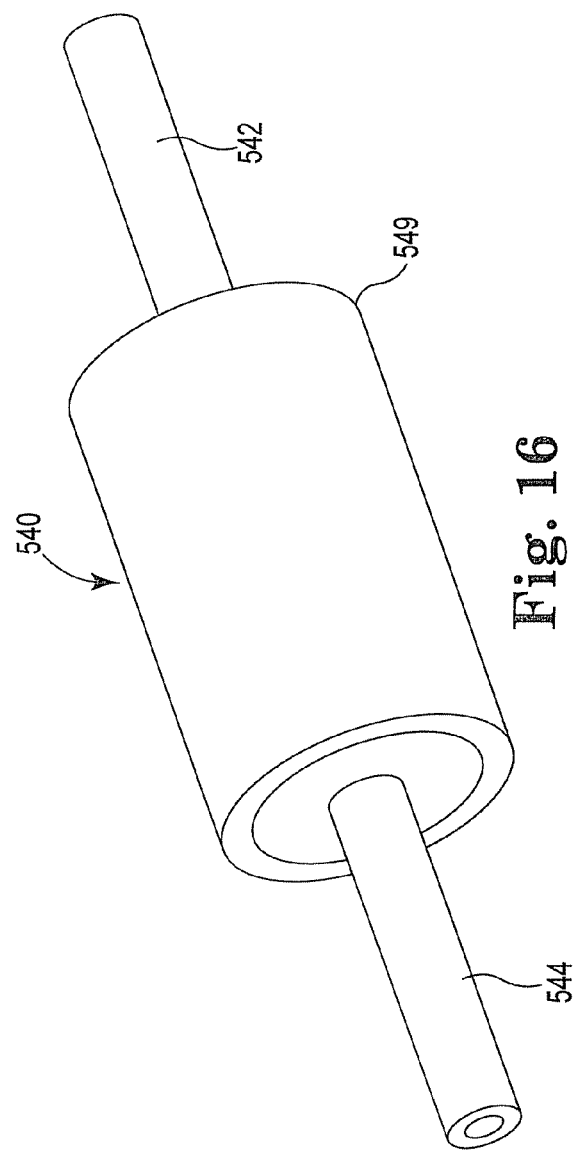
FIG. 16 is a side view of the flow restrictor of FIG. 15.
Figure 17:
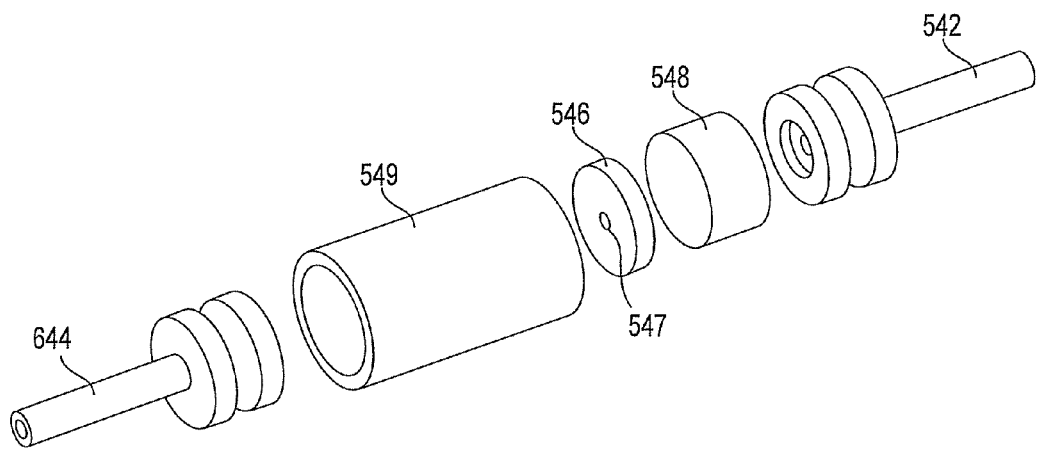
FIG. 17 is an exploded perspective view of the flow restrictor of FIG. 15.

FIGS. 15-17 depict an embodiment of a flow restrictor assembly that may be housed in an anchor body and used in a catheter system as described herein. FIG. 15 is a cross-sectional view of a flow restrictor assembly 540, while FIG. 16 is a perspective view of the assembled flow restrictor 540, and FIG. 17 is an exploded view of the flow restrictor 540.

The components of the flow restrictor 540 may, in some embodiments, be housed in a length of medical tubing 549 (e.g., urethane tubing), although other housings could also be used. Flow inlet 542 of the flow restrictor 540 may be defined by a tube having a lumen and may be coupled to, e.g., a supply catheter through a connector as depicted in FIG. 13. Flow outlet 544 may be defined by a tube having a lumen and may be, e.g., connected to a delivery catheter or a delivery catheter connector as discussed herein. In the embodiment shown, the flow restrictor 540 includes a body 546 that defines an orifice 547 through which the fluid being restricted flows. The body 546 may, in some embodiments, be in the form of a disc-shaped ruby body. In some embodiments, the bodies used in a flow restrictor such as restrictor 540 may have a thickness of 0.010 inch+/−0.001 inch (0.25 millimeters+/−0.25 millimeters) and include a generally circular orifice forming an opening having an inner diameter of 0.0004 inch+/−0.0002 inch (a 10 micron) inner diameter. If the body 546 is in the form of a disc, it may, in some embodiments have an outside diameter of 0.060 inch+/−0.0005 inch (1.5 millimeters+/−0.013 millimeters).

The flow restrictor 540 may also include a filter 548 located between the body 546 and the flow inlet 542 (such that it is located upstream of the body 546 in the intended use of the flow restrictor). The filter 548 may be, e.g., a porous 2 micron titanium filter, although any filter with suitable characteristics may be used.

Figure 18:
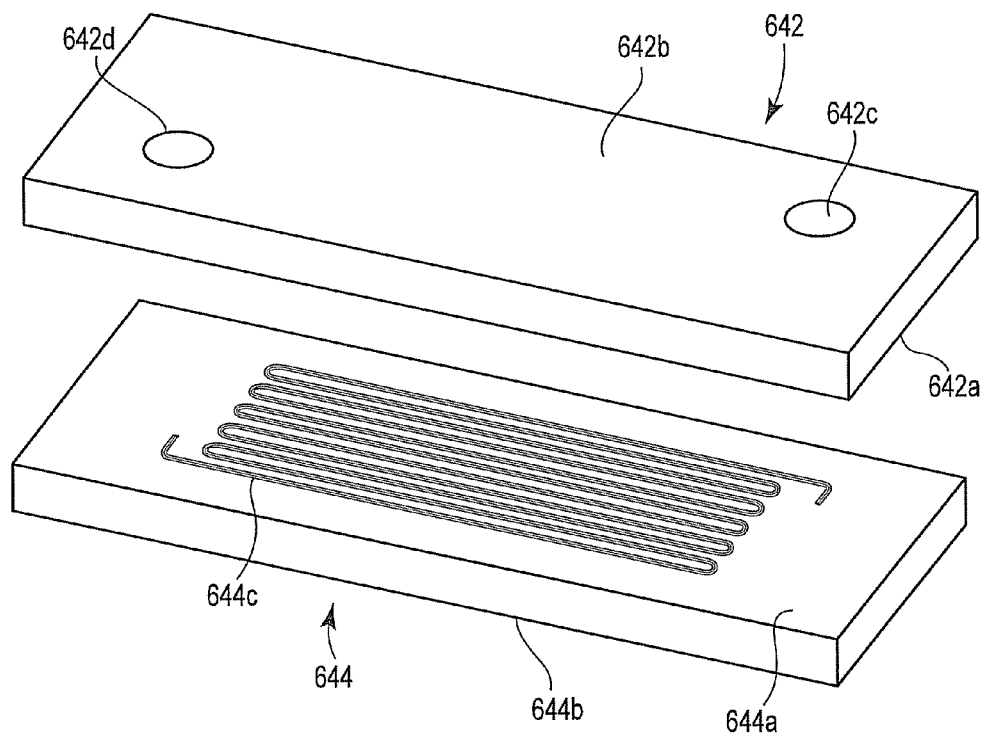
FIG. 18 is a perspective view of another illustrative embodiment of a flow restrictor that may be housed in an anchor such as that shown in FIG. 13.
Figure 19:
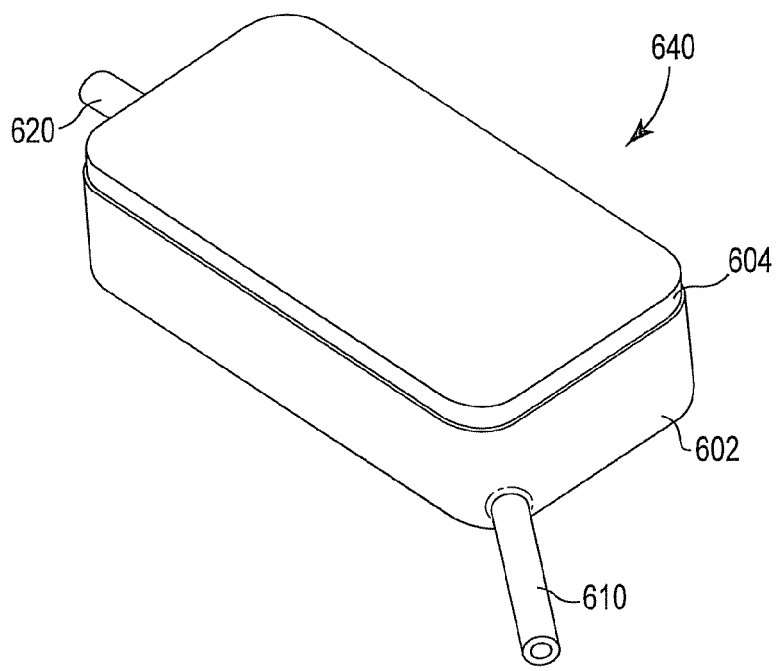
FIG. 19 is a perspective view of the flow restrictor of FIG. 18 within a housing.
Figure 20:
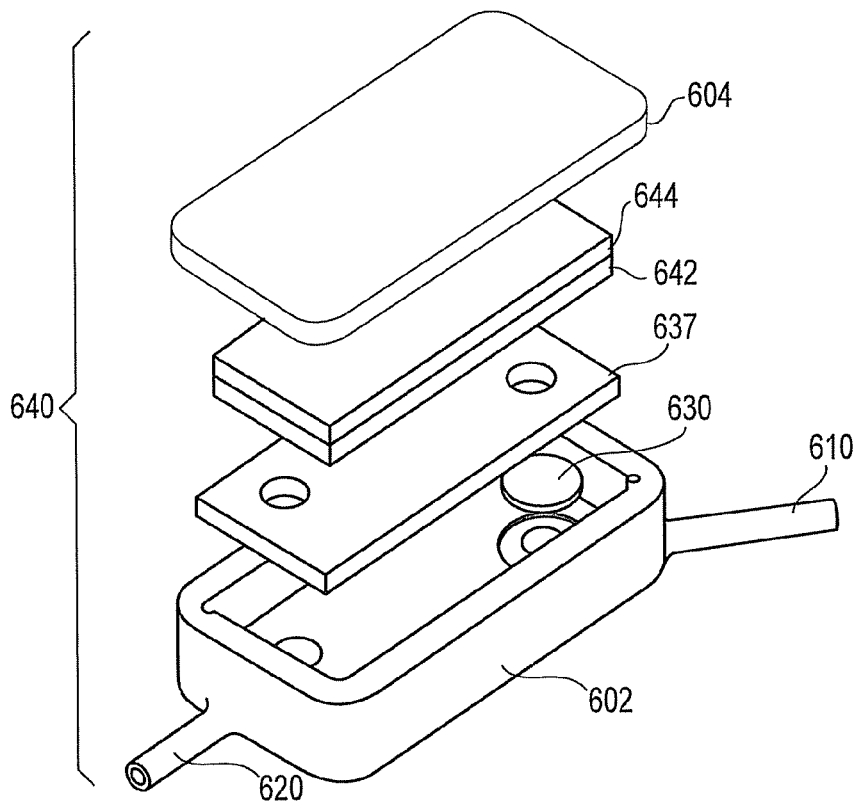
FIG. 20 is an exploded perspective view of the flow restrictor of FIG. 18.
Figure 21:
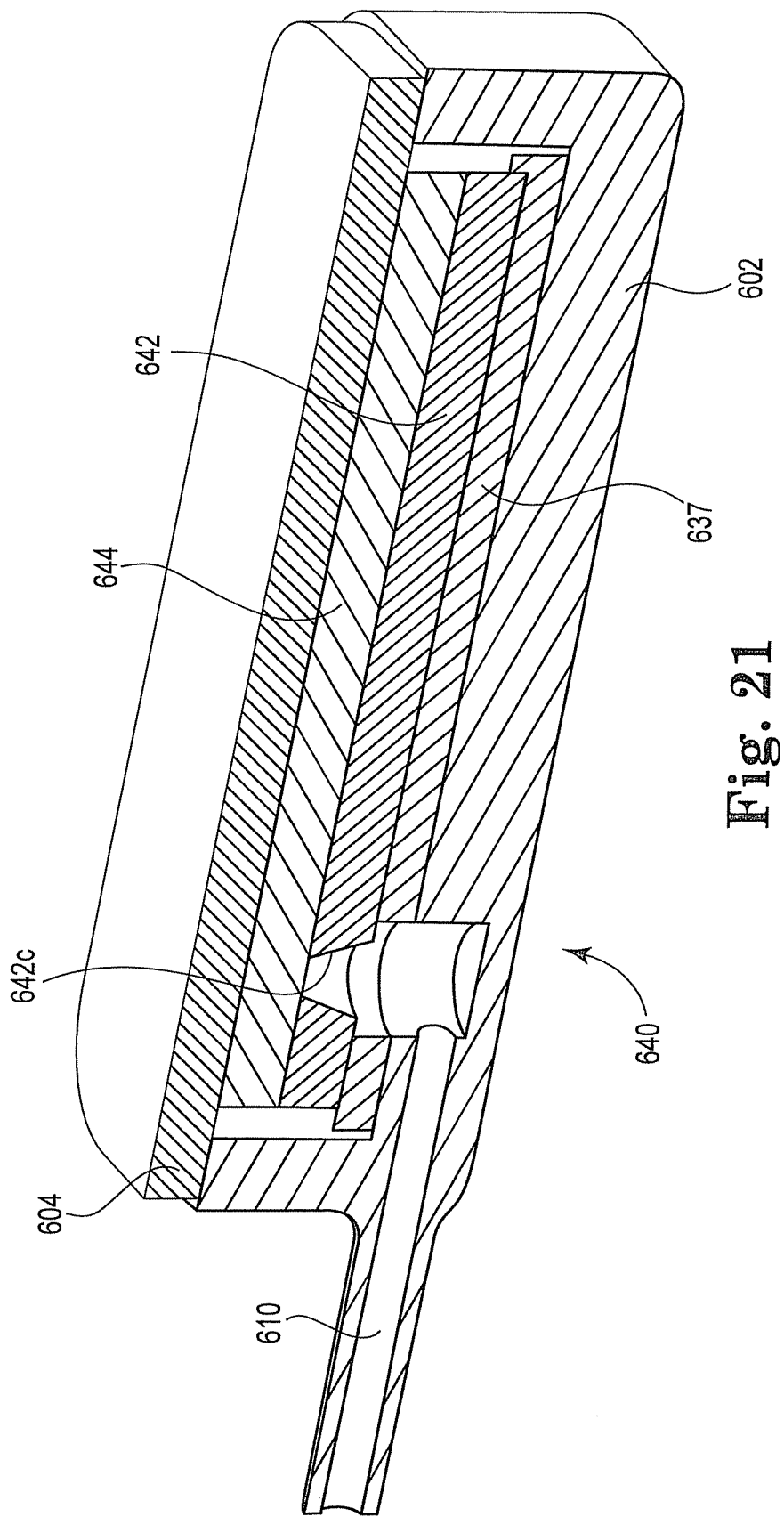
FIG. 21 is a cross sectional view of the flow restrictor of FIG. 18.

FIGS. 18-21 depict another alternative embodiment of a flow restrictor assembly 640 that may be housed in some embodiments of the infusion catheter systems described herein. FIG. 18 is an exploded perspective view of one embodiment of the chip assembly alone, FIG. 19 depicts the completed and assembled flow restrictor 640, FIG. 20 is an exploded view of the flow restrictor 640, and FIG. 21 is a cross-sectional view of the flow restrictor 640 taken in a plane that extends through the inlet 610 of the flow restrictor 640.

The flow restrictor 640 is described herein as having a housing with a flattened shape that includes two opposed major exterior surfaces defined by the base 602 and lid 604 (see, e.g., FIGS. 19-21), where each of the major exterior surfaces is significantly larger than the thickness or height defined by the side surface that extend between the two opposed major exterior surfaces. Flow restrictors with a flattened shape may be well-suited for use in a cavity formed in an anchor as described herein by providing the desired flow restriction in a form factor that complements the low-profile shape of the anchor in which it is located. In some embodiments, a flow restrictor with a flattened shape may form rectangular prismatic body, such as e.g., the flow restrictor 640 (which, although including rounded edges is generally in the shape of a rectangular prism).

Flow restrictor 640 includes a chip assembly that is formed by a first substrate 642 and a second substrate 644. The term chip assembly is used as it is formed in a similar fashion as that of forming a microchip. The substrates 642 and 644 may be constructed of, e.g., glass, silicon, or any other suitable material. The first substrate 642 has a first surface 642a and a second surface 642b. The second substrate 644 also has a first surface 644a and a second surface 644b. The first surface 642a of the first substrate 642 is positioned such that it faces the first surface 644a of the second substrate 644. The first and second surfaces of the first and second substrates 642 and 644 may preferably be planar. It may be preferred that the first surface 642a of the first substrate 642 has a shape that is complementary to the first surface 644a of the second substrate 644 (e.g., both surfaces may be planar, one surface may be convex and the other concave, etc.).

A continuous channel 644c is provided on the first surface 644a of the second substrate 644. When mated with the first substrate 642, the channel 644c provides a feature through which the fluid to be restricted flows. The amount of fluid (e.g., therapeutic agent or drug) that will flow through the restrictor 640 can be varied by varying the size (e.g., depth, width, etc.) and length of the channel 644c. In addition, more than one channel can be provided. The channel 644c may be formed by any suitable technique and/or combination of techniques, e.g., machining, etching (wet or dry), scribing, etc. In some embodiments, the first surface 642a of substrate 642 (which faces the surface 644a in which channel 644c is formed) may be flat or featureless, while in other embodiments, the facing surface 642a may also include features provided to help control fluid flow through the chip assembly.

Fluid is, in the depicted embodiment, delivered to the channel 644c through a first opening 642c that extends through the first substrate 642 from the first surface 642a to the second surface 642b. Similarly a second opening 642d extends through the substrate from the surface 642a to the second surface 642b. One or both of these openings may alternatively be formed in the second substrate 644 (i.e., the substrate that also contains the channel 644c). The openings 642c and 642d are preferably aligned such that they expose a portion of the channel 644c. If the channel 644c and the opening(s) are located in the same substrate, the channel preferably intersects or extends into the opening.

Some potentially useful dimensions for the channel 644c may, for example, be a channel depth of 15 microns, a channel width of 80 microns, and a channel length of about 45 millimeters. The overall length of the substrates in which the channel 644c and its mating surface are formed may be, e.g., 0.250 inch (6.35 millimeters), with a width of 0.100 inch (2.5 millimeters). All of these dimensions are exemplary only, in other words, they may be changed to achieve a desired flow rate, pressure drop, etc.

FIG. 19 shows the chip assembly of FIG. 18 within a housing that includes a base 602 and a lid 604 (both shown in FIGS. 20 and 21) wherein the base includes an inlet port 610 and an exit port 620. FIG. 20 shows an exploded perspective view of the various components of the flow restrictor 640 and FIG. 21 shows a cross-sectional view of the flow restrictor.

The opening 642c in substrate 642 of the depicted embodiment of flow restrictor 640 is proximate the inlet port 610. The inlet port 610 is in fluid communication (via opening 642c) with the channel 644c formed in the substrate 644. A filter 630 may be provided in the flow path between the channel 644c and the inlet 610 to capture particulates that could potentially clog or obstruct the channel 644c. In one embodiment, the filter may have a micron rating of 5 microns. As depicted in, e.g., FIGS. 20 and 21, the flow restrictor 640 may also include a compression seal 637 located in the flow restrictor 640 to help control fluid flow through the restrictor.

Other flow restrictors including chip assemblies that may potentially be used in the catheter systems described herein are described in commonly assigned U.S. Published Pat. App. No. 2007/0043335 A1 entitled MINIATURE PUMP FOR DRUG DELIVERY.

Another embodiment of the invention includes a method of delivering fluids from a single source through two or more delivery catheters or delivery pathways to two or more pre-determined target locations in a patient's brain, comprising the steps of connecting a proximal end of each delivery catheter directly or indirectly to a flow restrictor positioned in an anchor used to anchor the implanted delivery catheter in place, wherein the flow restrictor is also fluidly connected to a supply catheter and is located in the flow path from the fluid source to the delivery of fluid from the delivery catheter at the target location.

The complete disclosure of the patents, patent documents, and publications cited herein are incorporated by reference in their entirety as if each were individually incorporated.

Illustrative embodiments of infusion catheter systems and their components and methods of using them are discussed and reference has been made to possible variations within the scope of this invention. These and other variations, combinations, and modifications will be apparent to those skilled in the art without departing from the scope of the invention, and it should be understood that this invention is not limited to the illustrative embodiments set forth herein. Rather, the invention is limited only by the claims provided below, and equivalents thereof.

The invention claimed is:

1. An infusion catheter system comprising:
   a first delivery catheter comprising a proximal end and a distal end, wherein the first delivery catheter comprises a first delivery lumen extending from the proximal end of the first delivery catheter to a first infusion location located distally from the proximal end of the first delivery catheter, wherein the first infusion location comprises an opening through which fluid moving distally through the first delivery lumen exits the first delivery catheter;
   a second delivery catheter comprising a proximal end and a distal end, wherein the second delivery catheter comprises a second delivery lumen extending from the proximal end of the second delivery catheter to a second infusion location located distally from the proximal end of the second delivery catheter, wherein the second infusion location comprises an opening through which fluid moving distally through the second delivery lumen exits the second delivery catheter;
   a connector comprising a supply port, a first exit port in fluid communication with the first delivery lumen in the first delivery catheter, and a second exit port in fluid communication with the second delivery lumen in the second delivery catheter, wherein fluid entering the connector through the supply port exits the connector through either the first exit port or the second exit port;
   a first flow restrictor located between the first exit port of the connector and the first delivery lumen such that fluid flowing through the first exit port into the first delivery lumen must pass through the first flow restrictor, wherein the first flow restrictor comprises a disk-shaped body that comprises a first side facing the first exit port and a second side facing the first delivery lumen, the disk-shaped body further comprising an orifice formed through the disk-shaped body from the first side to the second side, wherein the orifice comprises a hole surrounded by the disk-shaped body, wherein fluid flowing through the first flow restrictor must pass through the orifice;
   a second flow restrictor located between the second exit port of the connector and the second delivery lumen such that fluid flowing through the second exit port into the second delivery lumen must pass through the second flow restrictor; and
   an anchor comprising an anchor body operable to secure to tissue at a selected location, wherein the anchor body comprises engagement surfaces configured to receive and immobilize the first delivery catheter as it passes through the anchor, wherein the first flow restrictor is housed in the anchor body.

2. An infusion catheter system according to claim 1, wherein the connector is located within a cavity in the anchor body.

3. An infusion catheter system according to claim 1, wherein the first delivery catheter and the second delivery catheter form a first pair of delivery catheters attached to the anchor, and wherein the system further comprises a second pair of delivery catheters, and wherein a separate flow restrictor is located in a fluid supply path to the second pair of delivery catheters.

4. An infusion system according to claim 1, wherein the anchor comprises a burr hole anchor operable to secure to bone surrounding a burr hole.

5. An infusion catheter system comprising:
   a first delivery catheter comprising a proximal end and a distal end, wherein the first delivery catheter comprises a first delivery lumen extending from the proximal end of the first delivery catheter to a first infusion location located distally from the proximal end of the first delivery catheter, wherein the first infusion location comprises an opening through which fluid moving distally through the first delivery lumen exits the first delivery catheter;
   a second delivery catheter comprising a proximal end and a distal end, wherein the second delivery catheter comprises a second delivery lumen extending from the proximal end of the second delivery catheter to a second infusion location located distally from the proximal end of the second delivery catheter, wherein the second infusion location comprises an opening through which fluid moving distally through the second delivery lumen exits the second delivery catheter;
   a connector comprising a supply port, a first exit port, and a second exit port, wherein the first exit port is in fluid communication with the first delivery lumen in the first delivery catheter and the second exit port is in fluid communication with the second delivery lumen in the second delivery catheter, wherein fluid entering the connector through the supply port exits the connector through either the first exit port or the second exit port;
   a first restrictor comprising a disk-shaped body that comprises a first side facing the first exit port and a second side facing the first delivery lumen, the disk-shaped body further comprising an orifice formed through the disk-shaped body from the first side to the second side, wherein the orifice comprises a hole surrounded by the disk-shaped body, wherein the disk-shaped body is located between the first exit port of the connector and the first delivery lumen such that fluid flowing through the first exit port into the first delivery lumen must pass through the orifice in the first restrictor; and
   a second restrictor comprising a disk-shaped body that comprises an orifice formed therethrough, wherein the disk-shaped body is located between the second exit port of the connector and the second delivery lumen such that fluid flowing through the second exit port into the second delivery lumen must pass through the orifice in the second restrictor.

6. An infusion catheter system according to claim 5, wherein the orifices in the first restrictor and the second restrictor comprise flow-matched orifices.

7. An infusion catheter system according to claim 5, wherein the system further comprises an anchor comprising an anchor body operable to secure to tissue at a selected location, wherein the anchor body comprises engagement surfaces configured to receive and immobilize the first delivery catheter as it passes through the anchor, and wherein the first flow restrictor is housed in the anchor body.

8. An infusion catheter system according to claim 7, wherein the connector is located within a cavity in the anchor body.

9. An infusion catheter system according to claim 7, wherein the anchor comprises a burr hole anchor operable to secure to bone surrounding a burr hole.

10. An infusion catheter system according to claim 5, wherein the first delivery catheter and the second delivery catheter form a first pair of delivery catheters, and wherein the system further comprises a second pair of delivery catheters, and wherein a separate flow restrictor is located in a fluid supply path to each delivery catheter of the second pair of delivery catheters.

* * * * *